(12) United States Patent
Erbs et al.

(10) Patent No.: US 8,361,788 B2
(45) Date of Patent: Jan. 29, 2013

(54) IMMORTALIZED AVIAN CELL LINES COMPRISING E1A NUCLEIC ACID SEQUENCES

(75) Inventors: Philippe Erbs, Dagneux (FR); Marina Kapfer, Schiltigheim (FR); Nathalie Silvestre, Ergersheim (FR)

(73) Assignee: Transgene S.A., Illkirch (FR)

( * ) Notice: Subject to any disclaimer, the term of this patent is extended or adjusted under 35 U.S.C. 154(b) by 18 days.

(21) Appl. No.: 12/667,240

(22) PCT Filed: Jul. 2, 2008

(86) PCT No.: PCT/EP2008/058472
§ 371 (c)(1),
(2), (4) Date: Dec. 30, 2009

(87) PCT Pub. No.: WO2009/004016
PCT Pub. Date: Jan. 8, 2009

(65) Prior Publication Data
US 2010/0197010 A1     Aug. 5, 2010

(30) Foreign Application Priority Data
Jul. 3, 2007   (EP) .................................... 07360030

(51) Int. Cl.
*C12N 15/85* (2006.01)
(52) U.S. Cl. ........................................ 435/325; 435/455
(58) Field of Classification Search .................. None
See application file for complete search history.

(56) References Cited

U.S. PATENT DOCUMENTS

| | | | |
|---|---|---|---|
| 5,879,924 | A | 3/1999 | Foster et al. |
| 6,872,561 | B2 | 3/2005 | Bouquet et al. |
| 7,572,438 | B2 | 8/2009 | Erbs et al. |
| 2008/0227146 | A1 * | 9/2008 | Sandig et al. ............... 435/69.1 |

FOREIGN PATENT DOCUMENTS

| | | |
|---|---|---|
| EP | 1528101 A1 | 5/2005 |
| WO | WO 97/44444 A1 | 11/1997 |
| WO | WO 99/54481 A1 | 10/1999 |
| WO | WO 2005/007840 A1 | 1/2005 |
| WO | WO 2005/007857 A1 | 1/2005 |
| WO | WO 2005/042728 A2 | 5/2005 |

OTHER PUBLICATIONS

Sorrell et al., "Targeted modification of mammalian genomes", Biotechnology Advances, 2005, pp. 431-469, vol. 23.
Ivanov et al., "Propagation of avian pox virus vaccine strains in duck embryo cell line—Dec. 99", Experimental Pathology and Parasitology, 2001, pp. 1-4.
Ivanov et al., "Establishment and characterization of a permanent duck embryo cell line", Experimental Pathology and Parasitology, 2000, pp. 1-4.
Guilhot et al., "The 12S adenoviral E1A protein immortalizes avian cells and interacts with the avian RB product", Oncogene, 1993, pp. 619-624, vol. 8, No. 3.
Erbs et al., "In Vivo Cancer Gene Therapy by Adenovirus-Mediated Transfer of a Bifunctional Yeast Cytosine Deaminase/Uracil Phosphoribosyltransferase Fusion Gene", Cancer Research, 2000, pp. 3813-3822, vol. 60.
Fallaux et al., "New Helper Cells and Matched Early Region 1-Deleted Adenovirus Vectors Prevent Generation of Replication-Competent Adenoviruses", Human Gene Therapy, 1998, pp. 1909-1917, vol. 9.
Graham et al., "Characteristics of a Human Cell Line Transformed by DNA from Human Adenovirus Type 5", J. gen. Virol., 1977, pp. 59-72, vol. 36.

\* cited by examiner

*Primary Examiner* — Celine Qian
(74) *Attorney, Agent, or Firm* — Buchanan Ingersoll & Rooney PC

(57) ABSTRACT

Immortalized avian cell lines containing E1A nucleic acid sequences are useful for the production of viruses and are particularly useful for the production of recombinant viral vectors which can be employed for the preparation of therapeutic and/or prophylactic compositions for the treatment of animals and more particularly humans.

13 Claims, 4 Drawing Sheets

Random insertion

Targeted insertion

SEQUENCE LISTING

```
<160> NUMBER OF SEQ ID NOS: 5

<210> SEQ ID NO 1
<211> LENGTH: 1027
<212> TYPE: DNA
<213> ORGANISM: Mastadenovirus
<220> FEATURE:
<223> OTHER INFORMATION: human adenovirus type 5

<400> SEQUENCE: 1
ccgggactga aaatgagaca tattatctgc cacggaggtg ttattaccga agaaatggcc     60
gccagtcttt tggaccagct gatcgaagag gtactggctg ataatcttcc acctcctagc    120
cattttgaac cacctaccct tcacgaactg tatgatttag acgtgacggc ccccgaagat    180
cccaacgagg aggcggtttc gcagattttt cccgactctg taatgttggc ggtgcaggaa    240
gggattgact tactcactttt tccgccggcg cccgttctc cggagccgcc tcacctttcc    300
cggcagcccg agcagccgga gcagagagcc ttgggtccgg tttctatgcc aaaccttgta    360
ccggaggtga tcgatcttac ctgccacgag gctggctttc cacccagtga cgacgaggat    420
gaagagggtg aggagtttgt gttagattat gtggagcacc ccgggcacgg ttgcaggtct    480
```

-continued

| | |
|---|---|
| tgtcattatc accggaggaa tacggggac ccagatatta tgtgttcgct ttgctatatg | 540 |
| aggacctgtg gcatgtttgt ctacagtaag tgaaaattat gggcagtggg tgatagagtg | 600 |
| gtgggtttgg tgtggtaatt tttttttaa tttttacagt tttgtggttt aaagaatttt | 660 |
| gtattgtgat tttttaaaa ggtcctgtgt ctgaacctga gcctgagccc gagcagaacc | 720 |
| ggagcctgca agacctaccc gccgtcctaa aatggcgcct gctatcctga gacgcccgac | 780 |
| atcacctgtg tctagagaat gcaatagtag tacggatagc tgtgactccg gtccttctaa | 840 |
| cacacctcct gagatacacc cggtggtccc gctgtgcccc attaaaccag ttgccgtgag | 900 |
| agttggtggg cgtcgccagg ctgtggaatg tatcgaggac ttgcttaacg agcctgggca | 960 |
| acctttggac ttgagctgta aacgccccag gccataaggt gtaaacctgt gattgcgtgt | 1020 |
| gtggtta | 1027 |

<210> SEQ ID NO 2
<211> LENGTH: 26916
<212> TYPE: DNA
<213> ORGANISM: Cairina moschata

<400> SEQUENCE: 2

| | |
|---|---|
| gctatcactc catttcaagg aagggcaaaa ggccggttca ataccaacat ctgtgtagct | 60 |
| aagtaggatg aaatagatta ggtgaccaaa atatctgctt attcagcagg tgttgatcca | 120 |
| caggaggttc tacgataaag ctccagtagg agttgtacca gcgtaattcc tggagggcag | 180 |
| caataagtcc accatctaca ctccacaaag tctgatcttt aggtacaaag agctgtgctg | 240 |
| atctagaatg atgtggttag actgaatctg gctctaaatt tctgttatta gagtattatg | 300 |
| tattattaag taagaggcct tgcttcttac tgctgcctaa atgaagatta actttacagt | 360 |
| gaagcagagt gagagatgaa ggggtgataa tgtgttttgaa atatcagact taatctggca | 420 |
| ggtgataatc agttcattcc aaaaacgtta atgtgctgaa tcagattgac aagaaaatga | 480 |
| atcctaatta gttgaaatta atctgaagag aactgaaagt acatcatagc aaatagtaac | 540 |
| tcttcttcca catcacaagg aacagattcc actgtgttag tgatggaggt ttatacaaaa | 600 |
| aaaaaaaaaa aagaaaaacc agaacagctc ttaatttata tacttattga agcagattct | 660 |
| atatatgcat atgtatgcac attcattaat cagcagtaca tctcaacccct taaaagatcc | 720 |
| tggagaactg ttgcttgtca aaaagcactc aggttaggct aacatttgca gcttttgctc | 780 |
| tagcatacat ttacattagg tgtaaagaca aggaatgtgt aaaagagggt aaatgcattc | 840 |
| ctatctacaa tgttatgtat attttgttcc tgttatattg gctttacttc caagttgta | 900 |
| gtttgcagta ttagtttctt tttattggta tccttgcata tatatatatt caataaatga | 960 |
| gttatgaatt tcatatttgc atatctgtcc tttttctgaa agtagaactt taaaactgac | 1020 |
| acttcagtgc ataaaagcag tgttccctat tgatgttaaa gtacctcgaa agttttacca | 1080 |
| gaagacaagt gagtgcatac ttaaagtatg ctacttactt ggtggtaact gcgtatttgt | 1140 |
| gcattgttcc tgactttgtg taatgggtaa gttgctttgt atttaccact tgctaataat | 1200 |
| gtgaagtggc tggctcacta aaggttgcca ttctcacctt tcaaggactt cttgaaggct | 1260 |
| gtgtcataat aatttagagt aagacagata ctgagagcgc agagtgtaat atagttatgt | 1320 |
| tgcagaagag cggatagaca caggatgcat gttagaacca tataaatgtg gtgtaaaaga | 1380 |
| tcagcaaaac gaagaattgc ttggaagatg cttggttttg tccaaataaa tagctgctga | 1440 |
| gagtgagaga gtgagtgagt aatattcagt atttttaaag tgtcgagaaa tgtaatgggg | 1500 |
| aaaaatttaa aataaatgtt ttttgtttgt tttaaaagga gctgtgtgct tttatgttga | 1560 |

-continued

```
catgttgatt taattactgc ggtaggtatt tactgtgccc tgggaaacgg tatccccagt    1620
caacacagac ttatttgtca ggaaaaaaat tgtcatagat catcttcaaa taagagttga    1680
caaataatca aatcttgatg gagtataatt attaatactg tgattacata tccatctttg    1740
caagggtttc ctgaaaaggt cagttttaag tcttctattg tcaaatctga tgtttggagt    1800
agttcgctac atggtgtttg atgccatgta aatagttacc agatagacgt tttattttat    1860
gtgctgtatg ttttgtttt tcattcagtc agctggaatc attgaaacag agaaggtttc     1920
tcaagaaata tcctgaacct gttttgtgga tgtcttcatt gcaatagctg gtcactgaaa    1980
tcttggaata acgacagagg aatccatagg cacaggacca aacaccttc attgtcctca      2040 tatagcgtga tgttagggca gagtggtgag tacttcagtg gctcctgtgt ccatgcttta    2100
atgaactcta cttaatctac catatgtaag agacttgcag cacaggcaaa acaagggaag    2160
ttatctttgt gcctagataa tgtaccacat atggtaaaca attttcaagc ctcagagaca    2220
aaagaaggat gctgtaaagt ctcaagtctc agcttgtgtc tctgtttcca ctttctgtt     2280 ctttctgttc agacctctgg gccagtaatt taaactggaa aattaatgga acagagaaac    2340
tgtttgtgag cctatagaaa gatcaaattg tgtcagagta atgttgctcc ttctacaccc    2400
agataaactt tttgagcaga ggagaagcag tgaacagagc tttactttca tgactttgca    2460
taagaaaaca tgggaatgtg gtccgagacc aatttaaaaa tagaggtttt gaaaacttgt    2520
ttggaaaaca aaacttgctt ggaaaaccct attcagagct gtgaatcatt cacagacaac    2580
ctcttagggt tgtagccact catcagctga atatgattca acgatatgct gaaaaaaaaa    2640
aacacaaaca ttgttgtgga atgtatgaac aggaatgtag tctgtaagat gcgtgtcttg    2700
gtccttcttc tttaggtaat agtagaacac ctttctggga aaatggtatc cagctgttgt    2760
aggcactgca ctccatggaa aatgtgaaga aagtggaaat aatccagaga aaagcaatga    2820
gagggatgac aggataaaaa atgagccttg cttttaaggtg atgagagaaa agtgtttttc   2880
aaatctgtaa gagagccaca gagaagaaag aaagaaacag ttctcatcat tgcaggtagg    2940
acaagaaaaa taggtttaag ttgctgcagg aagcctttag cttagacatc agaatgggta    3000
attgtccttg acagtaggaa gaattaagct gtagcatgca cttcctggag aggtcgtgga    3060
atctcaggaa ttaggtttta aagggaatat ttgtaggcat cttttggggc tggtgcaatt    3120
gtaggttgga ggtgctgggg ataaggctaa tggaaatccc taccagccac tctaaggcct    3180
tctgcaagga gtcagaacca cttttcggaa gtaaaactct gtactggcag aggtcctgtg    3240
cttgacctta aggctcagag ccatgcattt ccgttttcat cttttcactt aaaatagcac    3300
ttgtggtagt aataacatgc tcttgcggag tggcacaggt ctgcatggtt atgaactttc    3360
tgtcaccacc cagcaaatgg cattttccac tcttctgttt cagattttcg ggagtacttc    3420
cttactccca aattcctgat tgaatacgac tgaaaacttc aacacgtttt tagtgcacga    3480
agtgtacttt atacaaatgt gtgggactat tgcacacaac ttactgattt tcttcactgt    3540
gtgcacatgt gctctgtgat gatacagagt ttggggtgac tgaactgtta cccagtctttt  3600 accgaattag ggcagcgatc ttaaaccttc atctgaactt ttgctagaga tgatcttcta    3660
ttttgtttag acagggttct ctgcttgctt gcatttgttc taaaacgaca gtctggatga    3720
gaagaaacca accagggctg gcactgccct accttttatt ccctggatac tttacttggc    3780
acatcacttg gcacacatgc aatacccttt tttcaccccg gtacccaaag aaaagacgtg    3840
ctcctgcaca gactcagcca aattcctgcc tgccagtgga gggcgttaca gagggcttggg  3900 gcagagggag gaaactcact cccaaagcat atactaaaaa taggccaatg cattgcaaac    3960
```

```
agctttgctg tgagagcttc cttctggcat gtagccatgc agctgcctta tagttttgag   4020
cctagatacc tccaaaacaa aacaaaaagt cgctaaagtt aaatgcagcc agcagtgctt   4080
atagtcttga taatccctac agtgtatcaa ttttagtttc ttccagagtg caggtagttt   4140
actcaattta acttcaaatg tctgagttac accattgaca ccattgtcaa gactagtgct   4200
ggcaatccct gaagtctgcc aagttcaaag cagggaggag gcctttaaag ttgaaatact   4260
cgggtgacgt gtccaaaaag ttttcctgtg gctttcctgt ggagtaggaa ctgcagtagc   4320
taggttgcaa aaagttttta aactctccaa attgctgcta actaaacatc cttaaatcct   4380
gacatgagag tatgaaatga gaaagtcagt tccttgattt agactagctt gaaaagaata   4440 aacttttttgc acaggactcc ctggacagtt gggctggata atagaagtga ttcattcagg   4500
tcttgatgcc tacaagtttc ttgggttttg ccatattttc cagtgatttg tgacatcatt   4560
tttgccctaa aataaatcgc atcatgtcct gccgtatgtt ttgactatga aaatggaggt   4620
ttcggtttga ataccaaact tcgttgttac ttctttcaga ggctgttgat aaaggaaaac   4680
gtgaagcttt tatgtaaatg atcatgattt ctcatttgca tcaagaatat tttccaaaat   4740
agtagttaaa tccctccaat gattttcagc tatgtcacat aaatcaccga aaacacggta   4800
attttgcacg ggtgtttttt ctcccttttt ttattgtcta atactcagct tatatttgag   4860
tcttctgtat ccaattacct gatttgtgtg gcaattaaac agaagatcag cgtcattgta   4920
cttcacattc tttttaaact catcagtagt atgaccacac tagttggtct tgtaagtttg   4980
taatttaaga tgtgcctgga agggggttcaa agagacagga gcagtagtgt gtctcacttc   5040
cctttggaaa gcctttctga tactgtcaag caatatttac atcaaagggg aactgaattc   5100
tggtaaactt ttccagactc caagtaaacc gaacaacctg agatttagat aaaccttggt   5160
ggatttaaaa acttgatggt atcactgtct aagacttgtg ttagcccatc agatattgca   5220
gacgtatatt ttgaggaaag gctttcagtt aattgataaa attaagagca gagttttggc   5280
aaaaaaaacc gccatctctg tcagtactt catggcatct tgaatttctg cagttagagg   5340
tacaggtgct ctgttctgca attaacccgt gctgttaatt aaaatgtact gtttgctaaa   5400
tatgattagt gtctggagcc aggtagcttg aaaaagcttc aagattattt cttttttacca   5460 ggaccatcaa gttttttagcc ctcccttttag aggaaggttc agaggaggtc ctatttaatc   5520
tgtcccagaa gaaaggctat ttctccccct agaatggggc ttggcagtcc ttttcagagc   5580
acttttcatc cttgtctcat agggatttttt aaggacagat ttctgaaagg atttttccacc   5640 gggtaaagcg ggatcctgaa tgggtgacag ataatacgta ggaattctgg cttcctactg   5700
ccaggttgtt tatcttgaga tcttaaaaat ggacttattt cccttttttaa gtgtaaactg   5760 agttcttgag gcacctttttc cactgaagta tctgactttg cccttactgc ccatctcagt   5820
cttgcacatt taacccaaat tcagatccag ggtgtggtgt tactcctaga acagctctta   5880
ctgtttgagg atctgaatga ctattttgcc agcttgtgcc atacaactcg agaggacctg   5940
caaaggggag gggagtcctg atgggcagtt ccctcccagc ctggcatgcg cttcgtgtct   6000
ccgcttccct tataatctgc ccagaaaaga tttctgaaat acttgagcag ctgccacaat   6060
ctgcatggga ggcagcagcc ttggcatgtg agctctgcca cctgatgccc ggtctgtact   6120
gaggcagtgc cagctggatc tgcaagcctc agcgaataca gccttcgtca gcgagttctc   6180
tgatcagatt gctgccttgg agccttttgc tggtcttcct cagctcttct cctgttactc   6240
agatagcctt accacctcct ctcatcatct tttgagtttc tatcctcacg ttacagccag   6300
gtaagcccat ttacccatgc tgatatcaac aggttccaga ttttttaaaa aacaatcctg   6360
```

```
tctggctcac agctagggag cctctagtga cacagctaag tcccctgcag ccatttagaa    6420
atgtttctgg agggatgcag gtacgtcttg cactcaggtg cctaatgaaa gcagattgac    6480
ctgttcattc cttcgaaagc aactaagcaa agtggggaat cccatgtctc tgccccactt    6540
ctgtgttcct gacggcaaga cctcctgcca gcaccaaccg cctgtgtttg gagtcagcca    6600
gccttccgtt ctgactgaag ttgaaggtac agtacaaact gctggctaaa gaagctgct     6660
tgacttgctt ttttaggagg cttgtcttgt ggggaaaaaa aaaaaagta cagataaatt     6720
ctgctgattc cttctgagtc acccagcagc gatggcaaag ctaggagaaa aaatgggatc    6780
acagagggat tgatgaatgg acagtgagtg acctgaagat ctaactcaaa ggacgttact    6840
tcaagtgcaa gtgtcaacat ataaatgctg agttgttgtc tccaagtacc ccactgttgg    6900
ggtatcctgg ttaccaagca aggttttagt aagtctgttc gaaaagttac atacagctga    6960
cattcatgca ggccatgatt tgccaggcct gagctctgag gtattcctgg acggttagag    7020
aggataaaat aatttagaag tcaggaaacc actcagagac aaaccattat ttataaaatt    7080
attttgcctt ctaaaagatg tgcgttccag agaaatcaca acgttggctc caacctttt     7140
gcatcatcta gctagaaaat gtgcagcttc cagataccgc cagatcacct cccttgaccc    7200
tgccctggaa acatcaatgg ctcccatacc agtaagaaca aaactggtca tctactaaat    7260
ccgttgctga tctcagctaa ccaacttcct gtaatatcag caaatatttc tgcttttgta    7320
aatctgttct tccttccata atggggtgcc agcaggaatg cttgggatcc agaaatgcgc    7380
tggttggcag gaagaacaaa gaaattgttc acccagaagg gcaaaaaagg actaatgctt    7440
tcgtccgctt gggagaagtt gcacagaact tatgccaaca acttttgcac gcaatcagaa    7500
agatgccgct ggatgttact tttaatagca gacgttaata tcagttatta attagaaatg    7560
tcttcagtaa ccagactaaa agcagatcct gaaacactcc tgtggttgaa cagtctcttg    7620
acagacactg cccactgtcc agtaatgtca ggcgctctct gaacttgaca gggcagctgc    7680
tgttttccc agccttctgg aaataggcca gctctgacat gtttctgata ttagctgggt     7740
gtatttcatt ctgctgccct aggcagtttg ataaaggctc cttcctcctg ctccagagct    7800
aacccaccca aactgtagcc gagcacctcg ctgcaacaaa actgcactcg ctagggttct    7860
gcctgtttgc ttcattaaga tctgcttaaa ttgtttcgta caaaggaaca ctcaaactga    7920
tttctgagcc caaagtagca gtgctaggtg tacatcagga gttgtttggc atgaagaaac    7980
attgccatgg cactgtatga ataaagttat ttttaagaat cattatccct tccttgatac    8040
caagtctttta tgcggcagaa aatcaaactt ggtctccacc cttacagaaa gcagaggaat    8100
gctttcagct gatagttgct taagctagaa tataagaaac catgaatttc tgtgtgcact    8160
gcggcattgc ccttcattcc agacctacag aaaaaaacga cacttttgtt actatttttt    8220
tccttcccat atgagaccag gggagctacc caggcatttc cattcttata attttacctc    8280
aagatcaaat tttctccagg cagttaaagg cagctgcacc cggagacctc gctcagcctc    8340
cccttgcatc ccacggagct gcgtttagtg agaaacctcc cccgaggtga cgggctgcag    8400
gggacccctt cccacacgcg tccccgtccc ttttctcagt gcaaacgcag ccaccgcccc    8460
ttgaaccctc ctccgggctc tctcggttcg gcggaggcag gaggggggccg tgcccgccgc    8520
ccgggagctc ctcacagggc ccgggccccg ggcggagcg gccgcggcca tgttgagggc    8580
ggggagcgcg gaaggcggcg ccggggccgc tgcggggcgc ggcgcctccc cgctccccgc    8640
cgctcctcgc cgcccgcagc cgcaacaccg gcccggccc cggcgggccg cgccatggcg    8700
accccagcc cctgcatcgt ggtgagtgcg ggccggcgc tgcctcctcg gcctcccgct     8760
```

```
gggcccggcg tgcggtgaac ggggaggggg gaggcggctg cggggagccg gcggggggccg    8820
cccgtccccg tggggcgccc cgcgtggcgt ggagtcacct tgaggggctc gggctcccgc    8880
tgccctgcac ggccccgccc ggccccccagc gccctcctc ggctgccggc tcggtctcgc    8940
ctcctgcccg tgtcctgcc atggggccgg cggggtgttg gcaatttcgg ggcgctgctt    9000
gggcggctcg cggttgggag agccgcgggt gctgcctcag aaggcgccca gaaataactt    9060
ccaccagaaa taacttccac caggcaccga cccggcgtgg cacaacttcc tattcctgtt    9120
gctcctcaca gcgcgctcgg gaggtcgtgc tccgtgtacc aaaacctgcg agctcagcac    9180
ccgaactggg atgccttttg gaggaagacc ccgctgaggg tgtattttc atcatcagtg    9240
tgctctgcta agaatccttt tttttttaat tattattttt tttaaaccca gccccgggtg    9300
ccgtgagcgg tagcgtgaca cgcatgtggc gcctcgcggc ccacggccat gcctgccgtc    9360
aggctgtgcc cgcgcgcctg cctgtacttt ctcgctaaaa atccatctgt aaaacccacc    9420
gaacagcccg ctcagtacca aacgtagcct gcaaggctta gtggatgtgc tagatgtagt    9480
tatggggctg aaccgtagga aatttccgta gctgctgaga gggacccagc tcctgacacg    9540
cagcaggtca cgggctcggt gcctggcctg ctgcgagcag gggttgtgca ggggctgctg    9600
tggctgggag ggcaggcctg gctcccggcc aaaatcctca ttaccgcttg cgcaaccaaa    9660
aaacatgtaa acagctggct gatcacaggc aaggtaagtg cttccttggg cactgaaatg    9720
gaagcgtgat ctgcaccggc agcggagctg aggtggatgc ttaccatgcc tgccccgctg    9780
cattgccagc agcaggcttc agtgttcccc acaaacttct ttttacactg agcagccttc    9840
agctgcgtaa ccaacaagtg aagcgattca aaatatattg tcattttcaa gtggcagcgg    9900
ggctaaggtt caggggaagt ttttttcttgg tgcttttgga acaatatgcc ctgaaccaca    9960
gcagtggttg tataattacg tacataggca aacccccttgt cctaattaat acactcctgc   10020
taatgttgca agctgtttca tgtggaaaat ctgcccgtgc ggaacaggtt gctgaaacag   10080
ggctttaatt tctgattcta aagatcttga acctccactg tttccagatg gtggtcagag   10140
aaggcttgtt tcataggcac ataacttgtc ccgttaatat agctgtcttg tcttgtattg   10200
acagctggct tgtatgtttt gttgtgattc ggtgttgtgg agatttggaa gatgtccctg   10260
ttacaaggtc tgcttactta gttgcaaagg caggttttgc attacactgc tgaaatcaga   10320
gatgttgaaa agctgaaagc tgcttgatcc ttgtttattt atttatttt aaatgaaata   10380
agattatttg aggtgtagta atttcatttt ccccgctctc caatgggggg aaatgttgtt   10440
agggcttgaa atcatttccc ctccacatcg tgctgagcga cagctcatgt agcatttcag   10500
acaactcttg tgaactgtgg gttgtgcaag cttccacttt gtgctctgtt cagaaggaaa   10560
ataaggtgat cccaactagt gtaatggatt tggtagttta ttgagtaaag caaaggattg   10620
gcagtttctc actacaggct ttctataaga ctttgtagaa atctcacctt atttcctttt   10680
cagattgacg atgatgaaca aggttacgac ctggacttgt tctgcatacc taaacattat   10740
gcagatgatt tggaaaaagt ctatattcct catgggctca tcatggacag gtttgtttga   10800
cttcagacag tacactgctc cagctgattc catgacactg gaaaaaacaa tcttccagtg   10860
atagttttgc tgcctagtga ctgtctaaac agattacatt taattagaga ctaagaaata   10920
cacatgttaa ttaactctct cttgtttggc ttcaaagagt ttgtacattt gcagttacgc   10980
tattgtttgg aaatttgtca attctcaaag aaatttgtgg tacgtagcag tctgtgactt   11040
tctttacagt gtttctttga tgttttactt aaagtaatta gaacacatta cttgttgtgc   11100
tagttcaatc taaaaacagt tatagtctct caaacatctt taggatatta ataagagtag   11160
```

```
attattaatc acattatgat aagactttt  catgttcatg tggtagataa ctaacaccca   11220
atttccccct actgtctgcg aaagacatta gcctttgcaa ataccaatct gtcacttgtg   11280
gttgctgaaa tgtatgattt tctctggaag ttttatctcg tgatgagaaa tgggtacatg   11340
aacctataag gtgtttttgt tttactttgt gtaagtaaag tggaggagtt gctggagaca   11400
cagaaccact gaagagcggt tctgagtaga tcttgtgaat aggaatgctt ctagattttg   11460
catggtgctg tttgatcaga ttattacagt atttataata aaatgttttt taactttaca   11520
ctgaaagacc ctatatagga aagcattgga caaagtacag gtcattaagt agctgatgta   11580
aagtttgtaa tggcaggcat tctctgagaa acctgctgtc agctgctata ctgtaaatac   11640
ataccatgct ttctgaatta aattgcaaga taaatttaga aacaatgatc actgaaaaac   11700
tgttcagtgt tctcttgctc tgcttttattg gcattatatt ttgcagtcag gacaaattta   11760
ttcagcaaaa cataacgcta tagttgataa tttgagagtt ttcttgctcc tcagttagtg   11820
agagctgttg tcttttttggt tgtgctgatt tattttgctc tctgcatgga agctgaacct   11880
atctttggaa gaagaaaaca cccttatgtc tcttatctga cagtaaaaca attcagggtg   11940
ttcagatttg ctttggctga gtatgatgta tgaaaacaaa gaagtttggc agtgttactg   12000
ttagattaac cttggaacgc aaaactttgt tgaccaatag tgggttaaag tgactgaagc   12060
attaggcaaa tatttctgag caaaatatgc ttccgagttt gcatgtgttt gctgttgttg   12120
tttgcaatac aaaatactgc tgccatagta agcaaactaa atgtgttaca acagctaact   12180 ctctttttttt ttttttttgta taggacagag agactggcac gagaaattat gaagggcatg   12240
ggaggacatc acattgtagc tctctgtgta ctcaagggtg gctataaatt ttttgctgat   12300
ttattagact acatcaaagc actgaacaga aacagtgaca aatcaatccc catgactgta   12360
gacttcatta ggttgaagag ttactgtgta agtatctctg caataccatg caattttttct   12420 gtaaatttga ctaacttcaa attaacaaca gggatgattg agaattgcca acaaatgttg   12480
caaaagcttt gcctaagtac tgcctaaatt gtgctaattt tatacaaata gttaagacaa   12540
ttaaggggaa aaaagcagtc acaagctaac ttgttctttg tctatcttat atgatctggt   12600
ttctttcaga ctttatctcc tcggcccagt aaaatccaga gcaaagagac cctttccatg   12660
tcctttactt cttaaacaat ttcctctctg cccctgtcc cacctctaaa actgtggttc   12720
tagaataata cagaggatag tcctacaaat cttattacaa aaacttaact ctaggaatt   12780 tcatgtggct tagacatcac tcaccagata ggaaaacttg aaaactgtga gcatggttat   12840
atttgggttc cctacctcat cttttgtttg gctcaactga acaatgaatg gaatgaattg   12900
catttggcca tgaggaaata ctagattcat aaaaacagat ttatggttag cggccactga   12960
atatggtgct acctttttaaa gcctaggtct aggttgcctt ggctttatgc ttttggaaaa   13020
gaatttattt tcattttgca cacaagtatt taactttaca gggaaatgga gcatgaggta   13080
gtatgtaaga ttttataag ggaagcatta gattacattg tgcaggtcaa aggaggaagc   13140
agatgtatgt tagtactgta tgcttcctga ctcagcaaca gcctagtcta tgttttcaa   13200 gacagtattt gtgggtaatt tagattttt ccataagatc acctgtagtg tggaaataat   13260 taagttttttt gatttcaatt tacggtgtca aaataaattg cttcttaagg tcatgctgtt   13320
agttctgtgt ctcgatgact gtgttttcca gtcagtagta taagctactt gtcatggttg   13380
tggagtagtg cctgctgcag tagaaaaaaa tagattacta agttggaaac tcaactgcat   13440
tgttcattta attaaaccag agatagggt acttgcagat ttaggttgga ctgtagaaga   13500
gcttcaaaaa tgcgctgctg ctgttgagcg atctgtaaaa atttcacctc gttgagtggc   13560
```

```
aaagctcaga ccagtcagag tttggccagg cctgtttgca gaaaagctgt gccagctccc   13620
aaggtgtgtg tgcagtgatg tcctggggct acctggaaac caccgtcatg tctgcagagc   13680
gtgctgcagt gactcagctg cactctttaa agagaaggca aggccaggca gaaagggaca   13740
tgccagcctt tcgttacatc ttgcaagggg agagctgctt gacacacttt gtttctgctc   13800
cccacaaaag attcaggctc cctctaccag tccattcaac cacaaagcca ctacgtgccc   13860
acatacgctg tctgtaaaag ccacaacaga aaggtgaatg tctctattag aggataatat   13920
ttgaaagaat aggaaataac tcccaccttt tttggcgagg aaatttgtat tttctgcttt   13980
cttcaaggaa cacatccaat aactttggtt tatttaaaat ataaggacta caccttctg   14040 ctctctccac cttccgagta acttggaaca agctatggga taagtgttgt gaaacacctg   14100
gaaaaaatac tacattgcaa agcaaggctt attgtacagc atgttttat tgttcatctt   14160 tatgcattag gcatgtattg gttctgctgc ttttattttt tacaccgccc ccccaaacta   14220
tagtgctttt atattaatag gaaactgaac agcaaaataa ttacggaagt tttaattctc   14280
tttttgtagt aagaaggagt aaacaaagag aaaagcagag aaatttacac agaaaggagt   14340
gtaagcagaa tgttttccat gaggtgttgg cttcagggtt ttggttttgt cagccaattc   14400
tgtaaaggaa tgttttcttg ttctatatga ccgaggagct ccagttactt gatggcccca   14460
ctagcagatt attacgagca tttcatttct gtcaactctc taaggtagtt attaatatcc   14520
agacttacgt tctttagatt gcataacttg atagactggg taagactgtc ctaacacaaa   14580
catgcgtgta attgattcac ttagtttcc attattaatg gtgctggaat gttaaatctg   14640
ctctgtagtt ttcattcgtg ctttactaaa cggaggagtc agcattctta atgatgggaa   14700
aaccatcaca aaccgtaatg gacagttgaa agtagagcta gctctcttgt gattgttgtt   14760
ggatgcaatt actagatcac gctgcctgcc tttacagact gggtgaaaga tgttaaaaat   14820
accgtcgttg cataaacaaa gcagctgaac tcgtataatg gttctaaaat tgatgcgatt   14880
gatgttctat tcctatttga aattgatcat ttaatatttt caagcttatg ggttatttgt   14940
ttcataatgc aaagttcata ctatgattgc acccaaaaat aattctctaa gaatactgag   15000
atgatgaagc tgtgattaaa tgttgcttat aattcctgct ttcggagtcc ttacaaatga   15060
gttttaatga tctggcaagc tgttaagaaa ttgaaagata gtgtttgtga acagaaccag   15120
atctctgtat tcttgacaaa tagtttattt ttcttgtgct agaagaatgg cttttcacca   15180
gtttcctgca tgtaaagtta gagttaagca aaagttgctt atgtagtcac aaagggcagc   15240
caaaacacaa tggacgtgtt gcattgtcac tcagggaaat agggcttttc ggaggagtac   15300
tgcagcttta aggcaaaatc tagttaggct ggttgagaca gtattctgaa agatctcatg   15360
ttaactgagc cttatagcaa ataccatgag gaacttaaaa tgccttgtca ggggttacga   15420
tcttgcagca tgttattatt ttccagcaat gacaatgagg cagtgaaaac agatctaaac   15480
agtaaatctc taatgtgtta aatcacaaag cattaaagtc ttaccagtac tgaaatcaga   15540
aataatgctc ctgaagataa ttaaagtgtt gcttaattat taaacaaagt tctttccaat   15600
ggaaatctgg ttaaaaccag tgttggaaat ttgttaacca ttttgatcc tttaattgct   15660 cagaaactca gtacctgcat aggcgtgtag gtttatatgc cagcgaaggt ttatgttttg   15720
tgttaaaaaa tgtagcaatt tgcagggtgc ttggtgggaa gaagagggc agattttgtt   15780 ggttagattg ttttctctg ctgatcagtg tacttgagta tgcataaccc acagggttct   15840
gtagtgatct gtagttctgt gttgttattg tttgattata gtgtgttgct ttgtagccag   15900
agagatcacc aggaaactga tctgcatgca tgtactgaga ggactggtct atcatctgtg   15960
```

```
catggtgttt taatggaaca aatatctgta acatctttct ccatcttcct tctgtaagaa    16020
atggtgcttt ttacatcctt ccatggaaaa aggacgaaat tcttattagt gtaggaatag    16080
ataagagaga atcctgcaac ataaacaggg aaaagcttaa agctgtcatt taagataatt    16140
ttaagatatg atgaacgcag gaaatgcccc tcagcattac aaacacggtg cttaactgaa    16200
tcccattttc gtgattaatc taaccagtat ctctggcatt cagtagcagt ctgctgttta    16260
ctgggtcaag cagcagacat tttggacatc ctatttttgg acttttttcaa cacagtggta    16320 ttggttctgt tcactatagt tttctttaaa acatggggta aaactgtaaa ggcgcttttt    16380
ctaatgtgtt gtgcttgcct ttttttaat gttttgtcat gggaatctaa aatagaaagt    16440
atctgttagt ctcgttatct gcttttacat acctagagct gtcagcactt ctttatccta    16500
gagcattgac gtcactgtcc aagggatttt aatacatttt ctctttactg taatcccagt    16560
gtcacttatg gtgtgctcag tgtgtgtttc tctctaaacc atttacccct ttttgcatg    16620 tgataacact tctacttttt gtctgcaact ggtacagtat gaatatgtgt gtcagtgaaa    16680
acaggaagct gtatgtggcc gtctgttccc ctgtggtctc ctctctattg tatctgccat    16740
tttggggcgt ggggaaggaa ctgctctttt gctgcttgtc tgcatggtca tgcagtaagg    16800
ttgggcttca gactgaagcg gcaaaataat aaaggttttc taaagggaag atatgaagtg    16860
aagagctgtg agaatgaagt ttgaaaagtg gtatgaccct tcaaataaat gattaaattg    16920
taggataatg acatcatctg taagtagcac agtaatgagt atagcacaat taataagaac    16980
taggagacaa tgtcaaggtt taaagtcagc tgaatgactt taaataaact gcagagatct    17040
ggaggtaccc caggagttgt ttttaacttt cttatataac aaacagttca ctgatgctta    17100
catcaaagcc tagttttact aaagcaaaat gctgtacttc agtgatagga ttgtgtagct    17160
gtgtcgctgt ttaattacca caatgagtaa tttatcacta tttgtaaaat aggcaaaccc    17220
aagcttttct ggctattctt gtagcttata ttcttgttc ttaatctgtg ccttgtttgc    17280
tggctatttc attgttgtta tgattgctta ttttattca gagtaaggct ttctaaggca    17340
tcaaagttta aaatgtaaat taccagctat atagcagcgt acagcttgga aacttttttt    17400
ttttcctgtt ttccataccct ttaatgaata tgtaggaaat aatatttttt taatatacat    17460
gtgtgtatat ataatggtga cagatgagaa gtggtgcctg tatttatgta aatatttttt    17520
caaacaatct tttatctgaa ataccatctt tcagtttgat tacttgtaat ttcttagtta    17580
atagatgttg ctggtgcaat gcttctgaaa gctttggtat ttgtgggtta tgtactttgc    17640
agttttgata tttattagaa gaaaaattac tttaattctg gtaatactaa tgcttaccct    17700
gctctttctt gctagaatga tcagtcaact ggagatataa aagtcattgg tggggatgac    17760 cttcaacct tgactggaaa ggtatggcat gtcatatgtt taaagcaacc ccctcccccg     17820
cagaaaaaaa aatcctaaaa aatcctaaaa aaaacaaaa caaaccaaa aaaaacaaaa      17880 caaaacaaaa ccaaaaaaaa aaaaacacc aaagaaccaa ataattagag ttttagaaag     17940 gaaaaaaaa aaaaaagaaa gaaaactgta gtgtttcatt taaaatttag gttagaggtt     18000
ggacttgatg atcttgaggt ctcttccaac ctagaaattc tgtgattctg tgattctgta    18060
aaatattcac cattgtagag tggtggggtg cataagcccc accagagcca tcagtttagt    18120
ttgaacttca taacatatgt atgtatattc actgtcttca gtatcaggaa gtgttagagt    18180 tgttttctg cattgcctaa gaatagtctt gtcttggttg ttgttaacaa agtaccttta     18240
aaagagagta gcgttactta ttactgtgtt ggtgtttcat tgcaatagtg aacagagttg    18300
gtactgtcta gacatataac ttgcaggtta gggaataagg gtcctgttac aggcaatgaa    18360
```

```
gagacagaaa tgcagagaat gtaaattggg aatctgcttt tcttcagtgg ctgtgtagag    18420
atcattgagc tagatatctg tgggtaaaac atggatgcct cctgttctgt cagaacacat    18480
ggctttcccc ttctgattac acataaacag tctctgtccc atttcagtgt aagtgatgta    18540
ggtgtgacaa gacagtacat aactttatag tatgacattc tctgcattat aagaatttaa    18600
aggccacttt gtactcagca tgagatgttg aggcaagtct cattgtcaac taattgtcat    18660
tagagcatca gaaatgttaa ctaaatagaa ttcactgtta tgtgtcctaa catacataaa    18720
ccatggtaca aatatttaac tgcattgaaa ataaattat taagttatag gagacaatat      18780
atgtaagaaa tgctgtattc tttaaatgct aatggattct tcttttttttt tttttctttc   18840
caccagaatg ttttaattgt agaagtaagt attatgtttc actttgaagt tctaacgtgt    18900
gactggcaaa agaccttaaa cagaagttgg ttttaagtca gaaatcctac agtttctggt   18960
ttcaaggttt ttagtttctg actctaggcc tgaattatgc aagtggtctc tgaatttgaa    19020
attacctgtg ttttgaattc tcacatagca ttcaactata ccaaatttaa caaggaaaat    19080
atctgtgtaa aattgcttgc tgtttgcatt tgatttcagt tttctgtgat tctgtcaatt    19140
cttaaatgtc tttttttttt ttttaataat tcttattaag aagtagcctg agcaaagtgg    19200
tactaagtgt gttattgttc tgagtttata acagcaaact aggaaattaa actggagggg    19260
tagaaagaag ttcctagtag gaatatccta aaatacatgg gaaaacagag ctaaggccaa    19320
catctctgtg tacagtttct ttacaggcat ggagaatgtt gattcctaat ttgcattttg    19380
ataatgctta attcccattt ctctatcttg tcgtggttct ttgatactag gtacaataca    19440
cttcagtctg atttcctagt agctactgtt gcttaaatct tgcttccata cctctttgat    19500
gaacgatgtt gcttacattc agtaagtatg acttttacaa aggatgatct agaataagat    19560
cgctaacttg aggttggcaa agcagaagta ctaaacagga aaaatgaatg tatagaagta    19620
ataatgtctt cagactccaa atagtggaaa tggctttgtc cataagctat ggcaactgat    19680
tcagacacca aatgaaagga tgtttccttc tgtcattaaa tgtgtttttt ttatgtacgt    19740
cttttttttaa tttgagaagg ttatattatt ccataggaaa cacttttgac ctaaactgtt   19800
ttagttcagt tctaaaactc ctaccaaact agtatgtata cagcagtcat ctgtgtgacc    19860
ggtggcgtcc tttgaagtgt atttgcttca gataggcaga tgcatttaat tacgtatctg    19920
ctccatttca gatgaatgta tgtcttcaaa gtcccaggca gctaagtagg ttagtttctc    19980
atctgttcag tgaatcatct ctccagtgcc ttatatataa ttatacattg tcaaatatga    20040
accctttgac cagtcaccgt tttaactgtc aaacaatggg ggaaaacaaa caaacaaaac    20100
caaaaaacat tattataggc accagagcac ttaggttttc catacagaat cccttttgatg   20160
tataaaaaca aacaaacgaa aaagaagaaa agaatcccat cccttctgt gcaggggatg     20220
ggattaagat ggtgtgtcaa acatcatttt agtgtatata aatagaaact ttagaactgc    20280
acccagatat tgccagtgca gcttcttttgt ctttggattt ttttgggtct gtaatgtaag  20340
ttgcacttct ttttcctttta attgcattga tgggttgttc tgaatgtttt cccgtcttat   20400
tttctttctg ttgtatacat ctctctctga gttcaactgc aagactaatg ttccatttat    20460
aatactggaa ttaaacaatg tttgtcaaat agctacaagg aacacaagcc ataaactctt    20520
cagagggagc ctagaaggtc atagttcagt aactgctttc aaagtagtag ttatctacag    20580
ttttgactgt tgtgatcact ttactgagca taattgctta agcacaatat agcgttatgt    20640
atcacctgta tttgattatg aacattattt tgtcatattt ttgtgctatt acggatgagc    20700
aatttctgca gtaaaaactt gaaaatgcta ctctgaaaat tttaatattc tcacttacat    20760
```

```
gacactttta ttttcaggat ataattgata ctggtaaaac aatgaaaaca ttgctgtctc    20820
tactcaagca gtacaatcca aagatggtga aagtagccag gtaaacttct aaatgtgatt    20880
atttgtgctg tatttcaact tcagaatgac acacagtgga ataaaaatat aatatagaat    20940
atattcccat agaagagaaa caggaaggaa catttctgca ggaatcatac atgatggagt    21000
tagagttcag tatttgttta aactcaactt ctgcttgttg tgggagcata tgttcattaa    21060
ggctaacaga aatgctcttc tttccagtcc tattgcttga aaaatatcag tgccttatat    21120
tctagtaata tttgtggggt tttaccactg atctttaact taggtttaaa agcatatgga    21180
agaatttaaa tattttgggc ataaaaaaac acaacaacct ctcaaggtgg caggggtatt    21240
ttcaacacaa atttagttca taaatataaa ctttataaat ataagtttta actagagatt    21300
gggattaaaa aaaaaagtca gtggttgacg tctatggaca tacagtatct gaacatgttt    21360
cagtttgcaa cttcattttt tttcagtggt gtatctgcaa tggagacctt tggtctgcca    21420
gctttacttg tagaattaaa ttagtttgca ctaaacatta ccgtttatat agagtatata    21480
gtgtagctga gcctcagagg tcattctgtg agtcacccag ccatatgctc ttttaggctt    21540
ttctacttag ttgcatcttt aatcagttag ttatgaaacg ttttctaatt aaataactta    21600
cagttagtaa gaaatgttga gggtaatatt aaccaatatc aacattcctc ctacttcttt    21660
ttaaattgca tcttttatgc tcctatgctg tgattgtgta ttttacaata aaagcataat    21720
gattgctggg gattagagat aaaccagaac tgtgtgtaaa atctaatcag ttgtgttgcc    21780
ataacaatgt caaggcagtt gttagatgta ctagagcagc tcttcttgat gataatgtgg    21840
ggatgacctg ctgaaggtga ggttttttgtt ttttttttct ccgtggcctg cttaaatgta    21900 ccagattttta aatatttgtc actgaatagt accttaacgc tacagtgtac atcacaagta    21960
gaatgcagca tgaacaaagc ctagcttccg attgttttaaa cctgttgcag tttgggtctg    22020
ccgaagacct gagcaagtaa gcgtgatcgt gctggatagc tttaagtgtc atgctcttag    22080
ttcacttgcc tttcttttct taattttgtt ttctttctct ctgacaatta agcagttgta    22140
gcagggagat gtgaattaat gctaatgtga ttttgggttg gtttgatcaa gttttatgcc    22200
actactcaaa ttaagactct caactagaag tttcagaaac tgaatgtcta aagacagaca    22260
aatgtcagga tgatggggtc atcttctgaa agtgtgcaac tgaataatga gtgagtcaaa    22320
ttaaactaga aaggtatttc attctgctac agtacccca actctgcatg tctatgctttt    22380 ttacacctct gactattaat tctgtgaaag tggagctggt ttatatcagc ttatgatcat    22440
caaaaccaat tacattttct gtatgggggt aattagtact accagtggaa aaacagctga    22500
ggacatgttg cacaagtgca attgaggtta catttaacca gctgaacttt tgcttcataa    22560
cactaacgct tttgaaaaga cctcagctgg tctggctaga tcccaagttg tcacctcttt    22620
acctgcgagc taaactgatt gcacctgagg tttctaaaaa cacataaaac ctaattaagt    22680
cacttctggc aatgaaaatc cttccagtaa agtatctcac agcctctttg ctgcaaacat    22740
tttgtttatc ccttaggctg taaaccattc atgattctag gaagttttga gtttgtctat    22800
atgatcagct gcacctgcaa atgaataata tgtttaaaat gtatatagtt atgctgtcaa    22860
ttatacacat gtagtctcac tgaagtggaa ttcagctaat cttcgtgttt catataagtg    22920
aacctggtgt ttttccacgt ttcagtttta cattgttttt atttgacagt tgttggtaa     22980 aaagaactcc tcgaagcgtg ggatatcggc cagactgtaa gtgactttttt gacacccatt    23040 atcagttttt aaaatatgt tgtatatatg ttgatgtatt gtgtactctt tggtcaaagt     23100
ccaagggtgt tccaagtaag ttttcatgaa tggttttttga tttattttgc tcttatttgg   23160
```

```
gaagtttaaa tatttggaat gtattttgac agagttaata cagatttggt ctagtccttt    23220
ttttcttaac tttttgtggc attttattat acaaaaagga aactttgata ttttagtcca    23280
agttaatccc tcttcatatg gaaattctcc tagcttgcac gttaatcaaa tggtttggtc    23340
agcagaagtg tcatctttga cacttttggg agtgttccag gtgcctaaac atagccaccc    23400
agtgccactc ggatgtcccc agaaatgtaa tgggaccaca cagggtaaca gatctgatca    23460
aagtttacag tggtaagatg ttcaaagtag cacaaacccc atcttgttta agcatctgga    23520
ttactcctgt catgtcttct tgtctgtccc aagaccataa aggaaggaag agcatccaaa    23580
gcacacgggg gtgtcagtga tagcccctct tggcttggaa agggctacgt gtgctatccc    23640
tgtgccagag gttatttcct gttcatgtgg actgtgcgct ttcacaatgg aagtttaaca    23700
gaattgcatc ttctttcccc tcctttccaa gtttgcacag tattcttaaa ttgaaatttc    23760
tcagtgcctt gaaagcttaa ttcaggtgtt tccctcactc gaggatgcct ctctttcctg    23820
agatcttatt atgggtttag ctgggttaac agtctgcctt tctgagcatc ttgcagcaga    23880
tgacttgttt tgccatctgt ccagagacga cctgttcagt gcagaacccg tgagctctga    23940
aggcaagaga caacgcagca gcagagcttg ggcctgcctt ctgtccttgt atcatgaggc    24000
caagtagact ctaaacattg ccttattttt tccagaagcg tacacagtct ttcactggaa    24060
ttgtgtgatt tatctccgtt ttttcatta ctgagcctcg ctgtaaccag ggagagaaa     24120
acagcacagc tcgggagtct ttcatgttta gcataagggg agaaagcctt ctggaaacgt    24180
ccttaggttg tcttacagtg tgtgtggatg gcttggactg atacttcttg actatccaag    24240
gactgttctg ctagagccat gtccacttgg actatctgtg gaacagctga tgtgtttttt    24300
ttaggcagct tctatgggaa aaaaaaaaa cgaaacaaaa cacaacaaaa aacccgccgg    24360
tttctgaaaa gtgcaagtga caccgtaaat aagagagcgc cttttaccct gtggtcttca    24420
ctattctcta taccaagggc ttggcactta cagcgtgttg ctctgcagag ctgtcccgca    24480
gtcagagtat gtcctggtac accaggttgt tgtccacgag cagccagagg ggagtgaatt    24540
ttgtttggca ctgcctcaaa gacaaaggac tggttcccct gcggtaactc tggttcctcc    24600
tggtgttgac gtgttccatg cttactctcc cagctcttca caaagagccc agttgggctt    24660
gcacacctgt agttttgagg gagctgagag ctgaacctat ctgctcgtta tcccagaggt    24720
gaccttactt atagctgtgc ccaaggcgag ggcacactca cacaggtgcc acttttgaa     24780
taatactgtg agggtgacaa ctaaaacaaa ataaaatgct actgcttggg aaccagtaag    24840
taaatctatt tcattttgtt ttagttgaat taaatcaaca aatagagtta gaccattaac    24900
tagcttgaat attaatctcg ggatacttga atggaagaaa tgaaatgtta tgcttatatg    24960
tctataaaat tctagattct ctctgtaaaa aggtctagtg aactctagga agttcttttc    25020
taacatactg atgacttatg ttcttttca gttgttggat ttgaagtgcc agacaaattt    25080
gttgtgggat acgccctaga ttacaatgaa tacttcagag atttgaatgt aagtaacttt    25140
tcccgtatgt ttttgtccat ttaaaactag ggaggaggaa ggaagggaag tctcctcgca    25200
tcactctttc tcttctgtgt aaatcacagc tcatgtgcaa gcctgttcca ttagtgatgc    25260
aacgacgaga gcaaaggcta gaccagcaca acagtgtttt ggagctcata tgaaactaac    25320
ttttgttttg cttcatgcag aatggaggta ttctgcatga agctgtcagc tttgaaatac    25380
tgtggcagtc tgtatgaagt ttcttatctt accagacata tctgcaagaa acaagtgcat    25440
ttccttagtt acatcaaaat tagagaggag agacctggga tgttgagatg tttgcatttt    25500
atgctaggtc attattaatt tttcatctgg gtctcactaa ccttataaca gacatagggt    25560
```

```
aggagagaga gagaaagtcc agtgttgaga tctgtagaca aaaaaaaaaa gaagctaaag    25620
tttttctgca taaacaatat cacaaggctc ttcggtactg aaatgtgtat agcatgcttt    25680
tatttttttc agaagtgcat tattgaatac atctgtaaac atcatcctac attactttct    25740
aacaggagct tttatttttg ttttgttaca gcatatctgt gtgatcagtg agacggggaa    25800
gcagaaatac aaagcatgaa agcatagttc aagtgctctg atagcagagc tttgaaatgt    25860
tttgtttact gagtcctatc tttcacaggc ttcaactctg gtacaccagc taaaattgta    25920
gaattatcca cccccttgt catatgctta ctataactta ttgcatgtac aatatacaaa    25980
tcttgtcttg ttcatttata ttttagaaat gtaaacaatt agtgcaattc tgcactcctt    26040
attttgattt gcactatgac tctaccgact attgctgccc ctggttgggt tgtgctgttt    26100
gtgagctccg gagtctaact cttgcagtgg taaattgctt aaacctcatc aacccagaac    26160
tgaaatagtt caagtactgt aaatgtaaaa cactttatga tagggaagtc tattagtaat    26220 attttttaaaa tctgtaattt aagttttata ttttcatgaa caagtgtgat tgtgattaat    26280
ggatagttgc acctttgggt gttataaaac atgaggagca gccagttaca gtatctgtaa    26340
tcaccaagga gctgattcaa gcctcctgga gttgccttat cgctgtaaaa gtccgggtaa    26400
aaaaaatctt ttttttttta atttttttta tttttgagc taaaggaga tggaatgaca    26460 aagcagaatg tttaaaatct agtttaagtt gagctattca tttcttttgg atttttctt    26520 taaaaatacc catcagacag tgaaattgcc ttttaaattt aaacaatttt aatatatttt    26580
tgaagaagta ttgtaatgtt tactttataa gatctaaaaa acaaaaagta ctttaaataa    26640
aggctgtctc tttaaaataa gccccataca tctatgccac tcattctgta tattaaagtg    26700
ctcttgaaat tttcttagta atattttca taagtgtttc tgacagtgaa ggcagactct    26760
acgtttgtta tctttgtaga gcctttagtc agtattgtgc catctacaag agatgataaa    26820
ggcctgaggg aaagctatcg aaatacttgc gtattctata accaaactgg atttcagaga    26880
aaatgcacta agtagtgtcc cgtattctgt tttggc                             26916

<210> SEQ ID NO 3
<211> LENGTH: 3915
<212> TYPE: DNA
<213> ORGANISM: Cairina moschata

<400> SEQUENCE: 3
atggcgggcg cggagccctt cggcgccgtg ctgggcgccc tgcgggactg ctacgcgcag      60
gcggccccgc tggagacctt cctccggggg ctggggagga gcggcgccga ggaagccgag     120
gtggtgcggg acgacgacgc cgcctgctac cgcaccttcg tgtcccagtg cgtggtgtgt     180 gtccccacg gcgcccgcga catccccgg cccttcagct tggagcagtt atctagtcag      240
agcgaagtca tctcaagagt catgcagagg ctgtgtggga aaagaagaa gaacatcctc      300 acatatggat actccttgct ggatgaaaac agttctcact ccaaatcat gccgctctca      360 aacgtgtaca gctacctgcc caacaccgca acagaaacca tgcgtatcag tggcctctgg     420
gaaacgctgc tgagcaggat aggggatgac gtgatgatgt atttattgga gcactgtgca     480
atctttatgc tggttccccc tagtaactgt taccaagtct gtgggcaacc aatttatgaa     540
cttatttcgc aaaatgtaga atcagcccca gcgtttgtta acaacggct ttcaaagcac      600 aaacgtagta gcttgcttaa gtatacgcag aaaaggctaa cgtttcacag acagtatctt     660
tcaaagtcac gtcagtcgaa acgcaggcaa agacttgaag ctaatgtctc cagcatgaga     720
aataaaacca gcaataatat acaaagccta gggtccgctg ctctggaaaa acagagtagc     780
```

```
tccaatgcag gtttgtcagc tacagcacca tccttaaaaa ggaagcttgc tagggaacaa    840
ctggaagtca cggctaagag agcaagatta gaagagaaag agagggagga acaggcttgt    900
aatactgctc ctaatgtaaa ccagagtatt cccaagaggt atggaaccag ctgtgtagca    960
tcacgttctg taagtcttat taaagaaaaa tacatttctc aaagaagtaa cagtgatatg   1020
tctcgtcctt ctttagttca caattctcat catgggaaga agtctgtggc agacaaaagc   1080
tctttcctgc aaggagctga gagtaacaga catttaaagc ccagcattga aatgcaagca   1140
ggatccagca ggaagagagt agagatacac aggcctatac ctcggttgga ttggatacca   1200
atcgaaccgg cggaaagtag ttcttcagga cacaaaaagc aggaaagtcc cctagctcat   1260
ctggcagagg agttaccaaa tagggttttg ccatctacaa tatacattga caggaagttt   1320
cttctgtatt ctcgcaggta ctgggggaa cgtttcccaa aatccttcct attgaatcgc   1380
ctgaagggta gtgaggcagg tgtaaagcga ctaatagaaa cgatattctt aagccaaaat   1440
ccgtttgggc aaaagcgcaa ccaaggtctg ccacagaaaa aatggagaaa gaagaagctt   1500
cccaaacgct tctggagaat gagaagtacg tttcaaaaac tcttaaagaa tcatggaaag   1560
ttcccttacg tagcttttctt gagacaaaat tgccctcttc ggatatctga accatttttg   1620
ggaaaagcca agctgctcag tcgggcacct ttgcctgggc aagcagaggc tcacaagcaa   1680
gcagaacagc ttgggaagga gcctgctaag cgtgtggcaa gcagcagatg cgaatctggt   1740
cacaccaacg tgcccagcag cgtacgcgct cctctcgcag catctgcgtg cgtggagcca   1800 ggggggagg agcagatccc tgcagaggcg tctgattcag tcctcaggga gcttctcaag   1860
gagcactgca gccacttcca ggtgtacctc tttgtgaggg agtgcgtgga gcgggtgatc   1920
cccgccgagc tctggggttc aaaccataac aagcgccggt tcttcaagaa cgtgaaagca   1980
ttcatttcca tggggaagta cgctaagctt tccttgcagg tgttgatgtg aagatgaga   2040 gtaaatgact gcatgtggct tcgtctggcc aaaggtaatc actttgttcc tgcctctgaa   2100
caccgttacc gtgaagaaat tttggctaaa ttcctatact ggctgatgga tacgtatgtt   2160
gttgagttgc tcagatcatt tttctatatc accgagacca tgttccagaa aaatatgctt   2220
ttctactacc gaaagtgtat ttgggccaag ttacaggaca ttggaattag aaagcatttt   2280
gccaaagtac agctacgtcc tttaactgca gaggagatgg aagcgatcca tcagaaaaaa   2340
taccttccta tggcatcaaa gctccgtttc attcccaaag tcagtggact aagacccatc   2400
gtcagaatga gcggtgttgt tgaagcacaa acgttgagca aggaaagcag agcaaagaag   2460
atgaatcact acaacatgca actgaaaaat ctatttagtg tgttaaatta tgaacgaact   2520
ataaacacca gttacatcgg ctcttcagtg tttgggagag atgatatcta caagaagtgg   2580
aagacatttg ttaaaaaggt tcttaaatca gatggtgaaa ttcctcattt ctactatgta   2640
aaggccgatg tgtccagggc ttttgatagc attcctcacg ataaacttgt ggaagtgatt   2700
tcacaggtct taaaacctga gaaaaaaact gtctactgca tacggcgcta tgcagtggtt   2760
atgatcactg gaagtggaaa aaccaggaag ttatacagga acatgtttc tactttcaag   2820 gattttatgc cagacatgaa gcagtttgtg tcccggcttc atgagagtac ctcattgcga   2880
gatgcaataa tagttgaaca gagcttaact ttcaatgaga caagtgccag tctatttaat   2940
ttttttcttc aaatgctaaa taataacatc ctggaaattg agcgcagcta ctacttacag   3000
tgctctggaa ttccacaggg ctcccttttg tcaaccttgc tttgcagctt gtgctatgga   3060
gacatggaaa acaaattatt cagtgggta cagaaggatg gagtcctgat ccgtctcatt   3120
gatgactttt tgcttgttac accacactta acgcatgcaa gaactttcct aaggactcta   3180
```

```
gcaatgggca ttcctgagta tggcttttt g ataaacccca aaaagacggt ggtgaatttt    3240
tctgttgacg atatcccaga gtgttccgaa tttaaacagc tgccaaactg tcgtttgatc    3300
ccatggtgtg gcttattatt ggatacacag acacttgagg tttactgtga ttactccagc    3360
tattcctgta cttctatcag atcaagtctt tccttcaatt caaacagaac agctgggaaa    3420
aacatgaaac acaaattggt tgcagtcctt aaactgaaat gccatggctt gtttcttgat    3480
ttacagatca atagcgttaa aacagttttc attaatgtct acaagatatt tttacttcag    3540
gcttacaggt tccatgcctg tgttattcaa cttccattca accagaaagt taggaacaat    3600
cctgatttct tcctcagagt catcgctgag aatgcatcgt gctgctattc tatgctgaaa    3660
gctaaaaatc cagggtttac tttaggtaac agaggtgcat ctggcatgtt cccttctgag    3720
gcagcagagt ggctctgcta tcatgccttc actgtcaaac tgtcaaacca caaagttgtt    3780
tacaaatgct tgcttaagcc cctgaagttc tgtatgacac agctattccg gaagatccca    3840
aaggatacta aggcactact gaagacagtg acagaaccat ctatttgtca agatttcaaa    3900
gctatcctgg actga                                                     3915

<210> SEQ ID NO 4
<211> LENGTH: 18
<212> TYPE: DNA
<213> ORGANISM: Saccharomyces cerevisiae

<400> SEQUENCE: 4
tagggataac agggtaat                                                  18

<210> SEQ ID NO 5
<211> LENGTH: 18
<212> TYPE: DNA
<213> ORGANISM: Saccharomyces cerevisiae

<400> SEQUENCE: 5
atccctattg tcccatta                                                  18
```

IMMORTALIZED AVIAN CELL LINES COMPRISING E1A NUCLEIC ACID SEQUENCES

Figure 1:
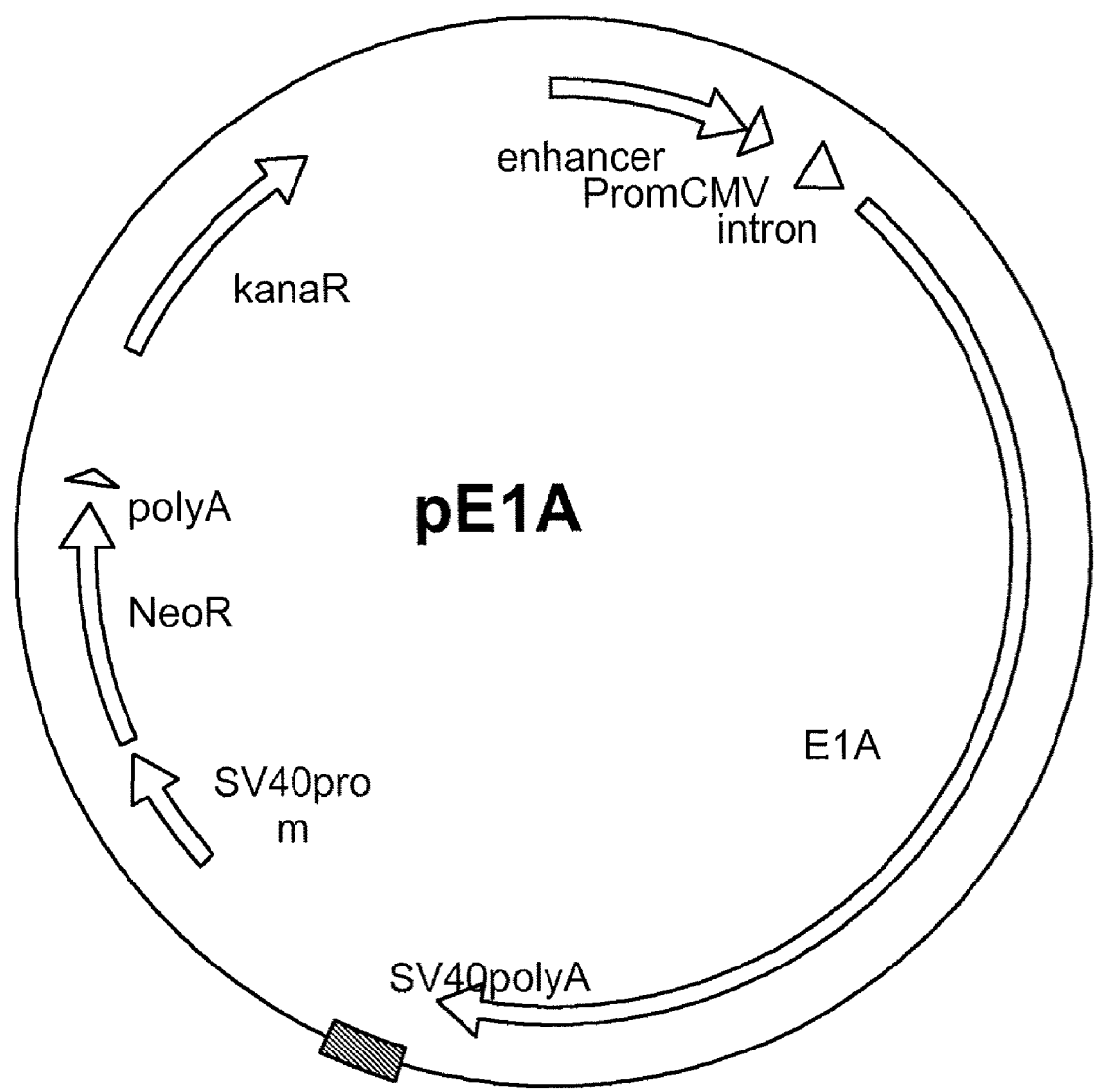

This invention relates to immortalized avian cells, and to the use of these cells for the production of viruses. The cells according to the invention are particularly useful for the production of recombinant viral vectors which can be used for the preparation of therapeutic and/or prophylactic compositions for the treatment of animals and more particularly humans.

Eukaryotic cell lines are fundamental for the manufacture of viral vaccines and many products of biotechnology. Biologicals produced in cell cultures include enzymes, hormones, immunobiologicals (monoclonal antibodies, interleukins, lymphokines), and anticancer agents. Although many simpler proteins can be produced using bacterial cells, more complex proteins that are glycosylated, currently must be made in eukaryotic cells.

Avian cells have been used for years for the production of viral vectors. For example, the Vaccinia virus used for preparing prophylactic composition for the treatment of Variola was cultivated on Chicken Embryonic Fibroblast (CEF). Avian cells are particularly useful since many virus used in pharmaceutical composition are able to replicate on them. More noticeably, various viruses are only able to grow on avian cells. This is for example the case of Mammalian Virus Ankara (MVA) which is unable to grow on mammalian cells. This poxvirus, which derived from a Vaccinia Virus by more than 500 passages on CEF was used in the early seventies for vaccinating immunodeficient peoples against Variola. Now, MVA is mainly used as a vector for gene therapy purposes. For example, MVA is used as a vector for the MUC1 gene for vaccinating patients against tumor expressing this antigen (Scholl et al., 2003, J Biomed Biotechnol., 2003, 3, 194-201). MVA carrying the gene coding HPV antigens are also used as a vector for the therapeutic treatment of ovarian carcinoma. More recently, MVA has been the vector of choice for preparing prophylactic treatment against newly emerging diseases or probable biological weapons such as west nile virus and anthrax.

With this respect, there is a growing need for virus production. For now, the most used MVA production process comprises a virus replication step on CEF. However the use of CEF is linked to various difficulties. Firstly, the preparation of CEF comprised many steps which have to be done manually.

Furthermore, this virus production process depends on the availability of eggs which may be totally disrupted in case of contamination of the breedings. This problem is more and more relevant with the spread of Avian Flu.

Additionally, many CEFs possess a reverse transcriptase activity (RT). RT is an enzyme necessary for retroviruses to reproduce. Retroviruses are found in many different species. RT is not infectious in humans or animals, and it has not been shown to cause any adverse health effects in people. Using a highly sensitive polymerase chain reaction (PCR) based assay, RT activity has been detected in minute quantities in vaccines manufactured with chick embryo fibroblasts. The source of the enzyme is probably a partial viral genome coding for RT, believed to be integrated into chick cells hundreds or thousands of years ago. Avian retroviruses that produce this RT are not known to affect humans. While the human immunodeficiency virus (HIV, the virus that leads to AIDS), is a retrovirus, the RT activity detected in vaccines is definitively not derived from HIV. Furthermore, the presence of RT does not confirm the presence of a retrovirus. Nevertheless, a cell line with no endogenous RT activity would be of interest.

In order to emancipate virus production process from the use of CEF, there is an increasing need for an avian cell line which would allow the replication and the production of the virus. Immortalized cell lines can be maintained or frozen from batch to batch on the production site and are always available for a new production process. Moreover as they are confined at the production plant, they are less subject to contamination by exogenous contaminant. Their use allows a drastic reduction of the manual manipulation needed for the production process. All these properties lead to a reduction of the price and of the duration of the production process as well as a diminution of the potential contamination.

Finally, cell lines can be fully characterized and are thus totally compliant with the good laboratory practice and the requirements of the different medical agencies.

Different avian cell lines have already been described. For example, DF1 (U.S. Pat. No. 5,879,924), is a spontaneously immortalized chicken cell line derived from 10 day old East Lansing Line (ELL-0) eggs. The cells are useful as substrates for virus propagation, recombinant protein expression and recombinant virus production. However, this cell line is susceptible to various virus such as Meleagrid herpesvirus 1 (Herpes Virus of Turkey), Fowlpox Virus, reovirus, Avian Sarcoma Leukemia Virus and Rous Sarcoma Virus.

Immortal avian cells can also be derived from embryonic stem cells by progressive severance from growth factors and feeder layer, thus maintaining growth features and infinite lifespan characteristic of undifferentiated stem). The only available avian cell line derived by this process is the Ebx chicken cell line (WO2005007840) which has been in contact with feeder layers from murin origin, raising additional regulatory questions like murin virus contamination and presence of endogenous retroviral sequences in chicken cells. Moreover this cell lines have been described in some conditions as unstable and differentiation-prone.

A duck embryo permanent cell line, free from endogenous avian retroviruses has also been established. The cell line, designated as DEC 99 (Ivanov et al. Experimental Pathology And Parasitology, 4/2000 Bulgarian Academy of Sciences) has been cultured over 140 consecutive passages and it is not tumorigenic for birds. The DEC 99 cell line is a standard cell culture system that has been used for research and can be applied for the needs of biotechnology. This cell line is a suitable model for studies in the field of cell biology, virology, immunology, toxicology and for the production of diagnostics and vaccines. The susceptibility of the permanent duck embryo cell line (CL) DEC 99 to infection with embryo-adapted avian poxvirus (APV) vaccine strains have been studied (Ivanov et al. Experimental Pathology And Parasitology, 4/6 2001 Bulgarian Academy of Sciences). The FK and Dessau vaccine strains of fowl and pigeon origin respectively have been used. The virus strains were consecutively passaged (13 passages) on primary duck embryo cell cultures (CCs). The adapted virus strains have been further passaged (12 passages) in the CCs of the DEC 99 cell line, where a typical cytopathic effect (CPE) was observed. The production of infectious virions was checked by inoculation of 11-day-old White Leghorn embryos, where typical pox proliferations on the chorioalantoic membranes (CAMs) were formed. In the DEC 99 cells the FK strain caused early CPE, compared to the Dessau strain and reached a titer of 106.25 CCID50/ml. The DEC 99-adapted virus strains induced typical cutaneous "takes" after vaccination of two-month-old chicks. Thus, the DEC 99, as a standard CC system appears to be suitable for production of vaccines against fowl pox. Nevertheless this particular cell line is slow growing after passage 40 and is unable to grow in suspension.

Nucleic acid sequences from the Early region of human Adenovirus 5 have already been used to transform some specific human cells in vitro (293 and PER. C6 cell lines; Fallaux, F. J. et al., Hum. Gene Ther. 9: 1909-17 (1998); Graham, F. L. et al., J. Gen. Virol. 36: 59-74 (1977)).

In general terms, the adenoviral genome consists of a double-stranded linear DNA molecule approximately 36 kb in length which contains the sequences coding for more than 30 proteins. At each of its ends, a short inverted sequence of 100 to 150 nucleotides, depending on the serotypes, designated ITR (inverted terminal repeat), is present. ITRs are involved in the replication of the adenoviral genome. The encapsidation region of approximately 300 nucleotides is located at the 5' end of the genome immediately after the 5' ITR.

The early genes are distributed in 4 regions which are dispersed in the adenoviral genome, designated E1 to E4 (E denoting "early"). The early regions comprise at least six transcription units which possess their own promoters. The expression of the early genes is itself regulated, some genes being expressed before others. Three regions, E1, E2 and E4, respectively, are essential to the viral replication. Thus, if an adenovirus is defective for one of these functions, that is to say if it cannot produce at least one protein encoded by one of these regions, this protein will have to be supplied to it in trans.

The E1 early region is located at the 5' end of the adenoviral genome, and contains 2 viral transcription units, E1A and E1B, respectively. This region codes for proteins which participate very early in the viral cycle and are essential to the expression of almost all the other genes of the adenovirus. In particular, the E1A transcription unit codes for a protein which trans-activates the transcription of the other viral genes, inducing transcription from the promoters of the E1B, E2A, E2B and E4 regions.

It was shown by Guilhot et al. (Guilhot, C. et al., Oncogene 8: 619-24 (1993)) that retroviral transduction of the 12S protein of E1A from Ad5 can lead to immortalization of quail cells. However, WO2005042728 disclosed that it is impossible to immortalize avian cells when the E1A gene is introduced by transfection of naked DNA instead of retrovirus infection. WO2005042728 further states: "that the extremely efficient and stable transduction via retrovirus infection creates a cell pool large enough to harbor individual cells with spontaneous genomic changes that have blocked apoptosis that normally is induced upon Retinoblastoma inactivation." (page 10).

The presence of retroviral sequences in the cells obtained by Guilhot et al. hinder the use of such cells for the production of biological product and more particularly for therapeutic compounds.

The inventors have surprisingly found that avian cells and more particularly, *cairina moschata* cells can be efficiently immortalized by E1A transfection with a non-viral vector.

In order to solve the different problems linked to the use of CEF and/or to the use of previously available cell lines, the present invention provides an immortalized avian cell comprising an E1A nucleic acid sequence characterized in that said cell is obtained by a process comprising the step of transfecting the cell with a non viral vector comprising said E1A nucleic acid sequence and wherein said cell does not comprise an E1B nucleic acid sequence.

The present invention also refers to a process for immortalizing an avian cell comprising the step of transfecting said cell with a non-viral vector comprising an E1A nucleic acid sequence and wherein said process does not comprise a step of transfecting said cell with an E1B nucleic acid sequence.

An immortalized cell, as used herein, refers to a cell capable of growing in culture for more than 35 passages.

The term passage number refers to the number of times that a cell population has been removed from the culture vessel and undergone a subculture (passage) process, in order to keep the cells at a sufficiently low density to stimulate further growth.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "E1A nucleic acid sequence" refers to nucleic acid sequence all gene products of the adenovirus E1A region, including the nucleic acid sequence coding the two major RNAs: 13S and 12S.

Preferably, the term "E1A nucleic acid sequence" refers to a nucleic acid sequence comprising a nucleic acid sequence which has at least 60% amino acid sequence identity to SEQ ID No:1. In a more preferred embodiment of the invention, E1A refers to a nucleic acid sequence comprising a nucleic acid sequence which has at least 70%, preferably at least 80% and even more preferably at least 90% nucleic acid sequence identity to SEQ ID No:1. In a more preferred embodiment, E1A refers to the nucleic acid sequence set forth in SEQ ID No:1.

As used herein, the term "E1B nucleic acid sequence" refers to all nucleic acid sequence of the adenovirus E1B region, including the nucleic acid sequence coding the 3 major polypeptides, of 19 kd and 55 kd.

As employed herein, the term "substantially the same nucleic acid sequence" refers to nucleic acid molecule having sufficient identity to the reference polynucleotide, such that it will hybridize to the reference nucleotide under moderately stringent hybridization conditions. In one embodiment, nucleic acid molecule having substantially the same nucleotide sequence as the reference nucleotide sequence set forth in SEQ ID No:1.

Hybridization refers to the binding of complementary strands of nucleic acid (i.e., sense:antisense strands or probe: target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (Tm) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5*Denhart's solution, 5*SSPE, 0.2% SDS at 42° C., followed by washing in 0.2*SSPE, 0.2% SDS, at 65.degree. C.

As used herein, the expression "non-viral vector" notably refers to a vector of plasmid origin, and optionally such a vector combined with one or more substances improving the transfectional efficiency and/or the stability of said vector and/or the protection of said vector in vivo toward the immune system of the host organism. These substances are widely documented in the literature which is accessible to persons skilled in the art (see for example Feigner et al., 1987, Proc. West. Pharmacol. Soc. 32, 115-121; Hodgson and Solaiman, 1996, Nature Biotechnology 14, 339-342; Remy et al., 1994, Bioconjugate Chemistry 5, 647-654). By way of illustration but without limitation, they may be polymers, lipids, in particular cationic lipids, liposomes, nuclear proteins or neutral lipids. These substances may be used alone or in combination. Examples of such compounds are in particular available in patent applications WO 98/08489, WO 98/17693, WO 98/34910, WO 98/37916, WO 98/53853, EP 890362 or WO 99/05183. A combination which may be envisaged is a plasmid recombinant vector combined with cationic lipids (DOGS, DC-CHOL, spermine-chol, spermidine-chol and the like) and neutral lipids (DOPE).

The choice of the plasmids which can be used in the context of the present invention is vast. They may be cloning and/or expression vectors. In general, they are known to a person skilled in the art and a number of them are commercially available, but it is also possible to construct them or to modify them by genetic engineering techniques. There may be mentioned, by way of examples, the plasmids derived from pBR322 (Gibco BRL), pUC (Gibco BRL), pBluescript (Stratagene), pREP4, pCEP4 (Invitrogene) or p Poly (Lathe et al., 1987, Gene 57, 193-201). Preferably, a plasmid used in the context of the present invention contains a replication origin ensuring the initiation of replication in a producing cell and/or a host cell (for example, the ColE1 origin may be selected for a plasmid intended to be produced in *E. coli* and the oriP/EBNA1 system may be selected if it is desired for it to be self-replicating in a mammalian host cell, Lupton and Levine, 1985, Mol. Cell. Biol. 5, 2533-2542; Yates et al., Nature 313, 812-815). it may comprise additional elements improving its maintenance and/or its stability in a given cell (cer sequence which promotes the monomeric maintenance of a plasmid (Summers and Sherrat, 1984, Cell 36, 1097-1103, sequences for integration into the cell genome).

The term "non-viral vector" excludes viral vectors, such as, for example vector deriving from a poxvirus (vaccinia virus, in particular MVA, canarypox and the like), from an adenovirus, from a retrovirus, from a herpesvirus, from an alphavirus, from a foamy virus or from an adeno-associated virus.

The present invention also relates to cells deriving from the cell according to the invention. As used herein, the term "derived" refers to cells which develop or differentiate from or have as ancestor a cell according to the invention.

The term passage number refers to the number of times that a cell population has been removed from the culture vessel and undergone a subculture (passage) process, in order to keep the cells at a sufficiently low density to stimulate further growth.

As used herein, the term "transfected" refers to the stable transfection or the transient transfection of the cell of the invention.

The term "stable transfection" or "stably transfected" refers to the introduction and integration of foreign nucleic acid sequence into the genome of the transfected cell. The term "stable transfectant" refers to a cell that has stably integrated foreign DNA into the genomic DNA.

According to a preferred embodiment of the invention, the avian cell of the invention derives from a cell of the Anatidae family or of the Phasianidae family. Among Anatidae, cells belonging to the *Cairina* or *Anas* genus are particularly preferred. Even more preferably, the cells according to the invention belong to the *Cairina moschata* or to the *Anas platyrhynchos* species.

Preferably, the cell according to the invention is taken from an embryonic organism. Methods allowing the isolation of cells from a living organism are well known to the one skilled in the art. For example, methods disclosed in example 2 can be used. According to a preferred embodiment of the invention, the primary cell is isolated from an embryo belonging to the Anatidae family which is between 0 and 20 days old, more preferably between 5 and 15 days old and even more preferably between 11 and 14 days old.

According to a preferred embodiment of the invention, the E1A nucleic acid sequence is inserted into a target DNA sequence of the cell according to the invention.

As used herein, a "target DNA sequence" is a predetermined region within the genome of a cell which is targeted for modification by homologous recombination with the vector. Target DNA sequences include structural genes (i.e., DNA sequences encoding polypeptides including in the case of eucaryotes, introns and exons), regulatory sequences such as enhancers sequences, promoters and the like and other regions within the genome of interest. A target DNA sequence may also be a sequence which, when targeted by a vector has no effect on the function of the host genome.

As used herein, "inserted into a target DNA sequence" widely means that the homologous recombination process which leads to the insertion of the immortalizing gene introduces a deletion or a disruption into the targeted DNA sequence.

To produce immortalized avian cell wherein the E1A nucleic acid sequence is inserted into a target DNA sequence, the vector used in the process according to the invention can further comprise two homologous sequences capable of homologous recombination with a region of a target DNA sequence native to the genome of said cell genome.

The presence of said homologous sequences allows the site specific insertion of the nucleic acid molecule of the invention into the target DNA sequence by homologous recombination.

The term "homologous recombination" refers to the exchange of DNA fragments between two DNA molecules at the site of essentially identical nucleotide sequences. According to this particular embodiment of the invention, within the vector are sequences which are homologous with sequence portions contained within the target DNA sequence. In a preferred embodiment of the invention, the homologous sequences in the transfer vector are hundred percent homologous to the region of the target sequence. However, lower sequence homology can be used. Thus, sequence homology as low as about 80% can be used.

The homologous sequences in the transfer vector comprise at least 25 bp, Longer regions are preferred, at least 500 bp and more preferably at least 5000 bp.

According to a more preferred embodiment of the invention, the nucleic acid molecule is surrounded by the homologous sequences in the vector.

As used herein "surrounded" means that one of the homologous sequences is located upstream of the nucleic acid molecule of the invention and that one of the homologous sequences is located downstream of the nucleic acid molecule of the invention. As used herein, "surrounded" does not necessarily mean that the two homologous sequences are directly linked to the 3' or to the 5' end of the immortalizing gene, the immortalizing gene and the homologous sequences can be separated by an unlimited number of nucleotides.

The one skilled in the art is able to choose the appropriate homologous sequences in order to target a specific DNA sequence into the genome of the cell to be immortalized. For example, one homologous sequence can be homologous to a part of the targeted sequence, wherein the other homologous sequence is homologous to a DNA sequence located upstream or downstream the targeted sequence. According to another example, one of the homologous sequences can be homologous to a DNA sequence located upstream the targeted DNA sequence, wherein the other homologous sequence is homologous to a DNA sequence located downstream the target DNA sequence. In another example, both the homologous sequences are homologous to sequences located into the target DNA sequence.

According to a preferred embodiment of the invention, the target DNA sequence is the HPRT (Hypoxanthine phosphorybosyl transferase) gene.

The genomic sequence comprising the HPRT promoter and the HPRT gene of *cairina moschata* is set forth in SEQ ID No:2. The sequence coding the HPRT start at the ATG codon in position 8695 of the nucleic acid sequence set forth in SEQ ID No:2, the sequence upstream this ATG codon is the HPRT promoter sequence.

The one skilled in the art is able to choose the homologous sequences necessary for the integration of the E1A nucleic acid sequence into the HPRT gene. As between the various members of a family, the genomic sequences coding HPRT are highly homologous, the one skilled in the art is also able to design the homologous sequences necessary to target the HPRT gene of every avian cells.

According to a more preferred embodiment of the invention, the homologous sequences are customized in order to insert the E1A nucleic acid sequence downstream the cell's HPRT promoter. In this particular embodiment, the nucleic acid molecule of the invention is operably linked to the cell's endogenous HPRT promoter. "Operably linked" is intended to mean that the E1A nucleic acid sequence is linked to the promoter in a manner which allows for its expression in the cell.

According to this particular embodiment, the homologous sequence, upstream the nucleic acid molecule of the invention, has preferably a nucleic acid sequence which is homologous with at least 500 contiguous by and more preferably at least 5000 contiguous by of the nucleic acid sequence starting from the nucleotide at position 1 and ending with the nucleotide at position 8694 of the nucleic acid sequence set forth in SEQ ID No:2, with the proviso that said homologous sequence is not homologous with the nucleic acid sequence starting with the nucleotide at position 8695 and ending with the nucleotide at position 26916 of the nucleic acid sequence set forth in SEQ ID No:2. Moreover, this upstream homologous sequence is preferably directly linked to the start codon of the E1A nucleic acid sequence. According to an even more preferred embodiment of the invention, the homologous sequence upstream the nucleic acid molecule of the invention consists in the nucleic acid sequence starting from the nucleotide at position 1 and ending with the nucleotide at position 8694 of the nucleic acid sequence set forth in SEQ ID No:2. The homologous sequence, downstream the E1A nucleic acid sequence, preferably has a nucleic acid sequence which is homologous with at least 500 contiguous by and more preferably at least 5000 contiguous by of the nucleic acid sequence starting from the nucleotide at position 10580 and ending with the nucleotide at position 18009 of the nucleic acid sequence set forth in SEQ ID No:2. And more preferably, said homologous sequence, downstream the E1A nucleic acid sequence, consists in the nucleic acid sequence starting from the nucleotide at position 10580 and ending with the nucleotide at position 18009 of the nucleic acid sequence set forth in SEQ ID No:2.

Accordingly, the present invention also relates to a avian cell comprising an E1A nucleic acid sequence characterized in that said cell is obtained by a process comprising the step of transfecting the cell with a non viral vector comprising said E1A nucleic acid sequence, wherein said cell does not comprise an E1B nucleic acid sequence and wherein said E1A nucleic acid sequence is operably linked to the cell's endogenous HPRT promoter.

According to a preferred embodiment, the vector used in the process according to the invention comprises a first selection marker, wherein this first selection marker is a positive selection marker and wherein said first selection marker is surrounded by the homologous sequences comprised in the vector. With this respect, the homologous recombination process which occurs between the vector and the genome of the cell leads to the integration of the E1A nucleic acid sequence and of the first selection marker. When the transfer vector is circular, "surrounded" means that the first selection marker and the E1A nucleic acid sequence are positioned in the same section of the vector, said section being delimited by the homologous sequences.

As used herein, the term positive selection marker notably refers to a gene encoding a product that enables only the cells that carry the gene to survive and/or grow under certain conditions. Typical selection markers encode proteins that confer resistance to antibiotics or other toxins, e.g., ampicillin, neomycin, methotrexate, or tetracycline, complement auxotrophic deficiencies, or supply critical nutrients not available from complex media. In a preferred embodiment according to the invention, the first selection marker encodes a protein that confers resistance to antibiotics.

The integration of the first selection marker allows the selection of the cells that have incorporated the E1A nucleic acid sequence. Accordingly, the process according to the invention can further comprise a step wherein said cells are cultivated in a medium which only allows the growth of the cells which have incorporated the first selection marker. For example in a medium which comprises an antibiotic.

According to a more preferred embodiment of the invention, the first selection marker, in the vector, is surrounded by sequences allowing its suppression. Said sequences allowing the suppression of the first selection marker do not surround the E1A nucleic acid sequence. When the vector is circular, the sequences allowing the suppression of the first selection marker, the first selection marker and the E1A nucleic acid sequence are positioned in the same section of the transfer vector, said section being delimited by the homologous sequences.

Sequences allowing the suppression of a nucleic acid fragment are well known to the one skilled in the art (Nunes-Duby, S. et al (1998) Nucleic Acids Res. 26:391-406). These sequences can be recognized by one or more specific enzymes which induce the suppression of the nucleic acid comprised between said sequences, these enzymes are called "recombinase". For example, three well-known recombinases allowing the suppression of a nucleic acid fragment are the FLP, ISCE1 and Cre recombinases.

A typical site-specific recombinase is Cre recombinase. Cre is a 38-kDa product of the cre (cyclization recombination) gene of bacteriophage P1 and is a site-specific DNA recombinase of the Int family. Sternberg, N. et al. (1986) J. Mol. Biol. 187: 197-212. Cre recognizes a 34-bp site on the P1 genome called loxP (locus of X-over of P1) and efficiently catalyzes reciprocal conservative DNA recombination between pairs of loxP sites. The loxP site consists of two 13-bp inverted repeats flanking an 8-bp nonpalindromic core region. Cre-mediated recombination between two directly repeated loxP sites results in excision of DNA between them as a covalently closed circle. Cre-mediated recombination between pairs of loxP sites in inverted orientation will result in inversion of the intervening DNA rather than excision. Breaking and joining of DNA is confined to discrete positions within the core region and proceeds on strand at a time by way of transient phosphotyrosine DNA-protein linkage with the enzyme.

Another site-specific recombinase is the I-SceI. Other intron-homing endonuclease, for instance I-TliI, I-CeuI, I-CreI, I-PpoI and PI-PspI, can also be substituted for I-SceI in the process according to the invention. Many are listed by Belfort and Roberts ((1997) Nucleic Acids Research 25:3379-3388). Many of these endonucleases derive from organelle genomes in which the codon usage differs from the standard nuclear codon usage. To use such genes for nuclear expression of their endonucleases it may be necessary to alter the coding sequence to match that of nuclear genes. I-SceI is a double-stranded endonuclease that cleaves DNA within its recognition site. I-SceI generates a 4 bp staggered cut with 3'OH overhangs.

The enzyme I-SceI has a known recognition site. The recognition site of I-SceI is a non-symmetrical sequence that extends over 18 bp.

```
                                         (SEQ ID NO: 4)
        5' TAGGGATAACAGGGTAAT3'

(SEQ ID NO: 5)
        3' ATCCCTATTGTCCCATTA5'
```

Another site-specific recombinase is the FLP recombinase. Flp recombinase recognizes a distinct 34-bp minimal site which tolerates only limited degeneracy of its recognition sequence (Jayaram, 1985; Senecoff et al., 1988). The interaction between Flp recombinase and a FRT sequence have been examined (Panigrahi et al., 1992). Examples of variant FRT sequences are given by Jayaram (1985) and Senecoff et al. (1988), and an assay for Flp-mediated recombination on different substrates is described by Snaith et al. (1996).

Accordingly, the process according to the invention can further comprise a step consisting in suppressing the first selection marker from the genome of said primary cell. In order to suppress said first selection marker, the cell is transfected by the gene coding the recombinase specific for the sequences allowing the suppression of the first selection marker. Methods and vector able to transfer said gene into the cell are well known to the one skilled in the art, for example, the method disclosed in example 4 of the present application can be used. Vectors previously described can also be used.

According to a preferred embodiment, the vector used in the process according to the invention comprises a second selection marker which is not surrounded by said homologous sequences, wherein said second selection marker is a negative selection marker. Said second selection marker is particularly useful when the vector, used in the process according to the invention, is circular. The presence of said second selection marker allows the destruction of the cells in which the homologous recombination process has lead to the introduction of the section of the transfer vector that does not comprise the E1A nucleic acid sequence. When the vector is circular, the fact that the second selection marker is not surrounded by said homologous sequences means that the second selection marker and the E1A nucleic acid sequence are not positioned in the same section of the transfer vector, said section being delimited by the homologous sequences.

Accordingly, the process according to the invention can further comprise a step wherein the cells are cultivated in a medium which only allows the growth of the cells which have not incorporated the second selection marker. Said step can be made simultaneously with or separately from the step wherein said primary cells are cultivated in a medium which only allows the growth of the cells which have incorporated the first selection marker.

According to a preferred embodiment of the invention, the vector comprises a third selection marker wherein said third selection marker is a negative selection marker and wherein said third selection marker is located between the sequences allowing the suppression of the first selection marker. This means that the step consisting in suppressing the first selection marker will also lead to the suppression of the third selection marker. The presence of the third selection marker allows the destruction of the cells in which the first selection marker is present. When the vector is circular, the fact that the third selection marker is located between the sequences allowing the suppression of the first selection marker means that the third selection marker and the first selection marker are positioned in the same section of the transfer vector, said section being delimited by the sequences allowing the suppression of the first selection marker.

As used herein, the term negative selection marker notably refers to a gene encoding a product that kills the cells that carry the gene under certain conditions. These genes notably comprise "suicide gene". The products encoded by these genes are able to transform a prodrug in a cytotoxic compound. Numerous suicide gene/prodrug pairs are currently available. There may be mentioned more particularly the pairs:

herpes simplex virus type I thymidine kinase (HSV-1 TK) and acyclovir or ganciclovir (GCV) (Caruso et al., 1993, Proc. Natl. Acad. Sci. USA 90, 7024-7028; Culver et al., 1992, Science 256, 1550-1552; Ram et al., 1997, Nat. Med. 3, 1354-1361);

cytochrome p450 and cyclophosphophamide (Wei et al., 1994, Human Gene Therapy 5, 969-978);

purine nucleoside phosphorylase from *Escherichia coli* (*E. coli*) and 6-methylpurine deoxyribonucleoside (Sorscher et al., 1994, Gene Therapy 1, 233-238);

guanine phosphoribosyl transferase from *E. coli* and 6-thioxanthine (Mzoz and Moolten, 1993, Human Gene Therapy 4, 589-595) and cytosine deaminase (CDase) and 5-fluorocytosine (5FC).

FCU1 and 5-fluoro-cytosine (5FC) (WO9954481).

FCU1-8 and 5-fluoro-cytosine (5FC) (WO2005007857).

Said third selection marker allows the selection of the cells in which the suppression of the first selection marker has occurred. Accordingly, the process according to the invention can further comprise a step in which said cell is cultivated in a medium which does not allow the growth of the cell comprising the third selection marker. For example, a medium, which does not allow the growth of the cells comprising FCU1 as a third selection marker, comprises 5-Fluorocytosine.

The first, second and third selections marker can be used separately. For example, the vector used in the process according to the invention can comprise the first and the third selection markers but not the second one, or the second and the third selection markers but not the first one.

According to a preferred embodiment of the invention, the E1A nucleic acid sequence, the first, the second and/or the third selection marker are placed under the control of the elements necessary for their expression in the cell to be immortalized.

The elements necessary for the expression consist of the set of elements allowing the transcription of the nucleotide sequence to RNA and the translation of the mRNA to a polypeptide, in particular the promoter sequences and/or regulatory sequences which are effective in said cell, and optionally the sequences required to allow the excretion or the expression at the surface of the target cells for said polypeptide. These elements may be regulatable or constitutive. Of course, the promoter is adapted to the vector selected and to the host cell. There may be mentioned, by way of example, the eukaryotic promoters of the genes PGK (Phospho Glycerate Kinase), MT (metallothionein; McIvor et al., 1987, Mol. Cell. Biol. 7, 838-848), $\alpha$-1 antitrypsin, CFTR, the promoters of the gene encoding muscle creatine kinase, actin pulmonary surfactant, immunoglobulin or $\beta$-actin (Tabin et al., 1982, Mol. Cell. Biol. 2, 416-436), SR$\alpha$ (Takebe et al., 1988, Mol. Cell. 8, 466-472), the SV40 virus (Simian Virus) early promoter, the RSV (Rous Sarcoma Virus) LTR, the MPSV promoter, the TK-HSV-1 promoter, the CMV virus (Cytomegalovirus) early promoter. The Cytomegalovirus (CMV) early promoter is most particularly preferred.

The present invention more particularly relates, but is not limited to a process for immortalizing a cell comprising the steps:
of transferring into an avian cell a vector comprising:
  an E1A nucleic acid sequence surrounded by homologous sequences.
  A first selection marker wherein said first selection marker is a positive selection marker and wherein said first selection marker is surrounded by said homologous sequences.
  Sequences allowing the suppression of the first selection marker.
  A second selection marker which is not surrounded by said homologous sequences, wherein said selection marker is a negative selection marker.
  A third selection marker wherein said third selection marker is a negative selection marker and wherein said third selection marker is located between the sequences allowing the suppression of the first selection marker.
cultivating said cells in a medium which only allows the growth of the cells which have incorporated the first selection marker.
cultivating said cells in a medium which does not allow the growth of the cells which have incorporated the second selection marker.
excluding the first selection marker from the genome of said cell.
cultivating said cell in a medium which does not allow the growth of the cells comprising the third selection marker.

The cell according to the invention can further comprise one or more nucleic acid sequence allowing the propagation of a defective virus. "Defective virus" refers to a virus in which one or more viral gene necessary for its replication are deleted or rendered nonfunctional. The term "nucleic acid sequence allowing the propagation of a defective virus" refers to a nucleic acid sequence supplying in trans the function(s) which allows the replication of the defective virus. In other words, said nucleic acid sequence(s) codes the proteins(s) necessary for the replication and encapsidation of said defective virus.

The cell according to the invention can also comprise a nucleic acid sequence coding a substance of interest. As used herein, a substance of interest may include, but is not limited to, a pharmaceutically active protein, for example growth factors, growth regulators, antibodies, antigens, their derivatives useful for immunization or vaccination and the like, interleukins, insulin, G-CSF, GM-CSF, hPG-CSF, M-CSF or combinations thereof, interferons, for example, interferon-$\alpha$, interferon-$\beta$, interferon-$\gamma$, blood clotting factors, for example, Factor VIII, Factor IX, or tPA or combinations thereof. "Substance of interest" also refers to industrial enzymes, for example for use within pulp and paper, textile modification, or ethanol production. Finally, "substance of interest" also refers to protein supplement or a value-added product for animal feed.

According to a preferred embodiment of the invention, the cell according to the invention also comprises a nucleic acid sequence coding a recombinant telomerase reverse transcriptase and more preferably, the recombinant telomerase reverse transcriptase described in EP 06 36 0047.2. In a preferred embodiment of the invention described in EP 06 36 0047.2, nucleic acid sequence coding the recombinant telomerase reverse transcriptase has at least 70%, more preferably at least 90%, and more preferably at least 95% nucleic acid sequence identity to the nucleic acid sequence set forth in SEQ ID No:2 of EP 06 36 0047.2. Preferred nucleic acid sequence coding the recombinant telomerase reverse transcriptase described in EP 06 36 0047.2 is as set forth in SEQ ID No:2 of EP 06 36 0047.2. Telomerase reverse transcriptase nucleic acid sequence SEQ ID No:2 described in EP 06 36 0047.2 corresponds to telomerase reverse transcriptase nucleic acid sequence SEQ ID No:3 in the present invention. As a consequence, according to a preferred embodiment of the invention, the cell according to the invention also comprises a nucleic acid sequence coding a recombinant telomerase reverse transcriptase and more preferably a nucleic acid sequence coding a recombinant telomerase reverse transcriptase having at least 70%, more preferably at least 90%, and more preferably at least 95% nucleic acid sequence identity to SEQ ID No:3. More preferably, nucleic acid sequence coding a recombinant telomerase reverse transcriptase is as set forth in SEQ ID No:3 (dTERT).

The cells obtained by the process according to the invention, the cell of the invention and the cells derived thereof are notably useful for the replication of a virus. Said viruses can be live, attenuated, recombinant or not. More preferably, said cells are particularly useful for the replication of poxvirus (vaccinia virus, in particular MVA, canarypoxvirus, etc.), an adenovirus, a retrovirus, an herpesvirus, an alphavirus, a foamy virus or from an adenovirus-associated virus.

Retroviruses have the property of infecting, and in most cases integrating into, dividing cells and in this regard are particularly appropriate for use in relation to cancer. A recombinant retrovirus generally contains the LTR sequences, an encapsidation region and the nucleotide sequence according to the invention, which is placed under the control of the retroviral LTR or of an internal promoter such as those described below. A retroviral vector may contain modifications, in particular in the LTRs (replacement of the promoter region with a eukaryotic promoter) or the encapsidation region (replacement with a heterologous encapsidation region, for example the VL30 type) (see French applications 94 08300 and 97 05203).

Adenoviral vector can lacks all or part of at least one region which is essential for replication and which is selected from the E1, E2, E4 and L1 L5 regions. A deletion of the E1 region is preferred. However, it can be combined with (an) other modification(s)/deletion(s) affecting, in particular, all or part of the E2, E4 and/or L1 L5 regions. By way of illustration, deletion of the major part of the E1 region and of the E4 transcription unit is very particularly advantageous. For the purpose of increasing the cloning capacities, the adenoviral vector can additionally lack all or part of the non-essential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, for example, Graham and Prevect, 1991, in Methods in Molecular Biology, Vol 7, p 109 128; Ed: E. J. Murey, The Human Press Inc).

Poxvirus family comprises viruses of the Chordopoxvirus and Entomopoxvirus subfamilies. Among these, the poxvirus according to the invention is preferably chosen from the group comprising Orthopoxviruses, Parapoxviruses, Avipoxviruses, Capripoxviruses, Leporipoxviruses, Suipoxviruses, Molluscipoxviruses, Yatapoxviruses. According to a more preferred embodiment, the poxvirus of the invention is an orthopoxvirus.

The Orthopoxvirus is preferably a vaccinia virus and more preferably a modified vaccinia virus Ankara (MVA) in particular MVA 575 (ECACC V00120707) and MVA-BN (ECACC V00083008).

The term "recombinant virus" refers to a virus comprising an exogenous sequence inserted in its genome. As used herein, an exogenous sequence refers to a nucleic acid which is not naturally present in the parent virus.

In one embodiment, the exogenous sequence encodes a molecule having a directly or indirectly cytotoxic function. By "directly or indirectly" cytotoxic, we mean that the molecule encoded by the exogenous sequence may itself be toxic (for example ricin, tumour necrosis factor, interleukin-2, interferon-gamma, ribonuclease, deoxyribonuclease, *Pseudomonas* exotoxin A) or it may be metabolised to form a toxic product, or it may act on something else to form a toxic product. The sequence of ricin cDNA is disclosed in Lamb et al (Eur. J. Biochem., 1985, 148, 265-270) incorporated herein by reference.

In a preferred embodiment of the invention, the exogenous sequence is a suicide gene. A suicide gene encodes a protein able to convert a relatively non-toxic prodrug to a toxic drug. For example, the enzyme cytosine deaminase converts 5-fluorocytosine (5FC) to 5-fluorouracil (5FU) (Mullen et al (1922) PNAS 89, 33); the herpes simplex enzyme thymidine kinase sensitises cells to treatment with the antiviral agent ganciclovir (GCV) or aciclovir (Moolten (1986) Cancer Res. 46, 5276; Ezzedine et al (1991) New Biol 3, 608). The cytosine deaminase of any organism, for example *E. coli* or *Saccharomyces cerevisiae*, may be used.

Thus, in a more preferred embodiment of the invention, the gene encodes a protein having a cytosine deaminase activity and even more preferably a protein as described in patent applications WO2005007857 and WO9954481.

In a further embodiment the exogenous gene encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

In a still further embodiment the exogenous gene encodes an antisense RNA.

By "antisense RNA" we mean an RNA molecule which hybridises to, and interferes with the expression from a mRNA molecule encoding a protein or to another RNA molecule within the cell such as pre-mRNA or tRNA or rRNA, or hybridises to, and interferes with the expression from a gene.

In another embodiment of the invention, the exogenous sequence replaces the function of a defective gene in a target cell. There are several thousand inherited genetic diseases of mammals, including humans, which are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumour-suppressor genes that have undergone mutation.

Examples of protooncogenes are ras, src, bcl and so on; examples of tumour-suppressor genes are p53 and Rb.

In a further embodiment of the invention, the exogenous sequence encodes a Tumor Associated Antigen (TAA). TAA refers to a molecule that is detected at a higher frequency or density in tumor cells than in non-tumor cells of the same tissue type. Examples of TAA includes but are not limited to CEA, MART-1, MAGE-1, MAGE-3, GP-100, MUC-1, MUC-2, pointed mutated ras oncogene, normal or point mutated p53, overexpressed p53, CA-125, PSA, C-erb/B2, BRCA I, BRCA II, PSMA, tyrosinase, TRP-1, TRP-2, NY-ESO-1, TAG72, KSA, HER-2/neu, bcr-abl, pax3-fkhr, ews-fli-1, surviving and LRP. According to a more preferred embodiment the TAA is MUC1.

The recombinant virus can comprise more than one exogenous sequence and each exogenous sequence can encodes more than one molecule. For example, it can be useful to associate in a same recombinant poxvirus, an exogenous sequenced coding a TAA with an exogenous sequence coding a cytokine.

In another embodiment of the invention, the exogenous gene encodes an antigen. As used herein, "antigen" refers to a ligand that can be bound by an antibody; an antigen need not itself be immunogenic.

Preferably the antigen is derived from a virus such as for example HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus (preferentially non structural protein from genotype 1b strain ja) and hepatitis E virus, or from other viral pathogens, such as Respiratory Syncytial Virus, Human Papilloma Virus (preferentially the E6 and E7 protein from the HPV16 strain) or Influenza virus, or derived from bacterial pathogens such as *Salmonella, Neisseria, Borrelia* (for example OspA or OspB or derivatives thereof), or *Chlamydia*, or *Bordetella* for example P.69, PT and FHA, or derived from parasites such as *plasmodium* or *Toxoplasma*.

FIG. 1: Vector comprising a gene coding the E1A nucleic acid sequence.

Figure 2:
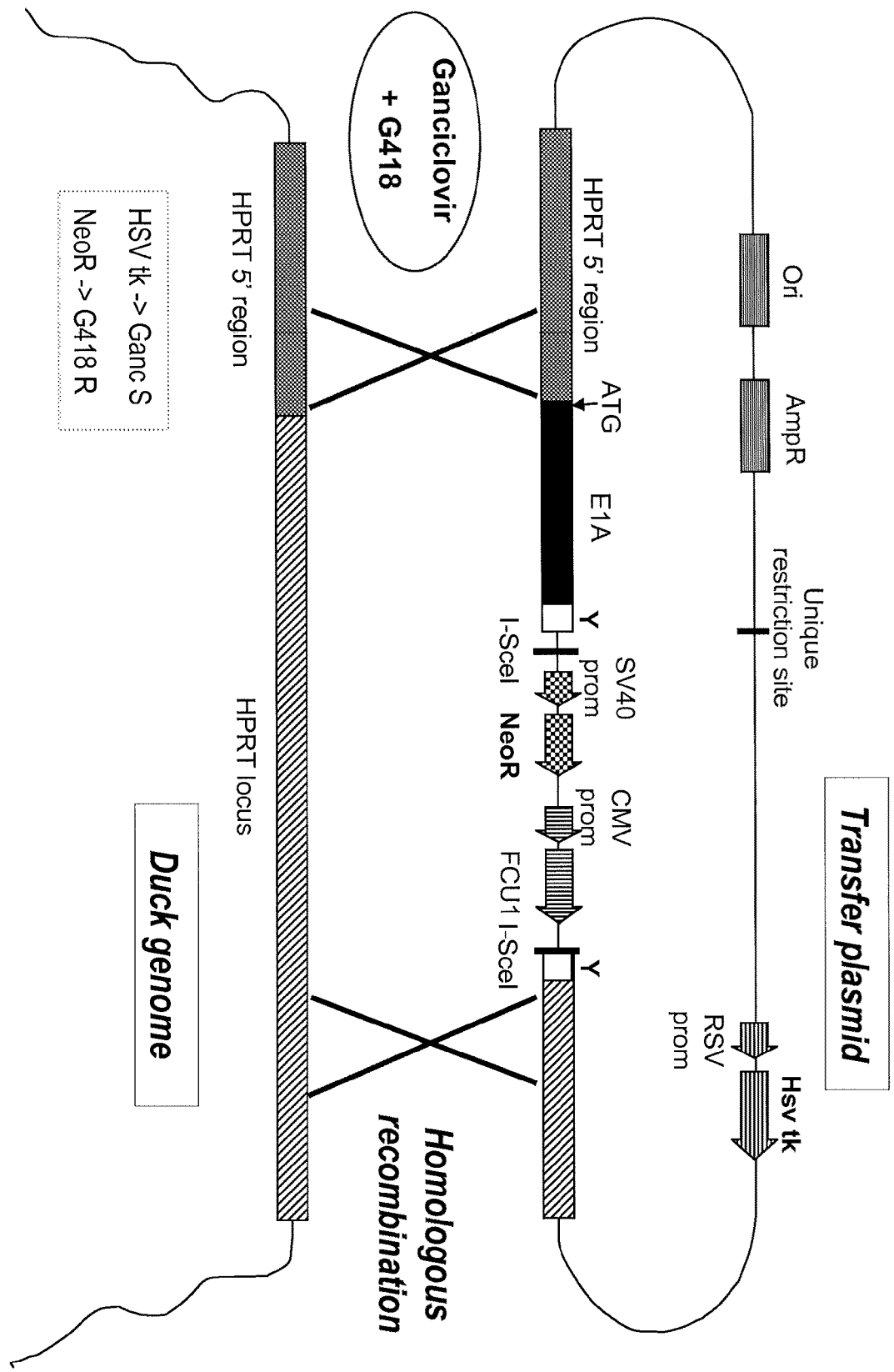

FIG. 2: Schematic representation of the site specific insertion of the E1A nucleic acid sequence into the HPRT gene.

Figure 3:
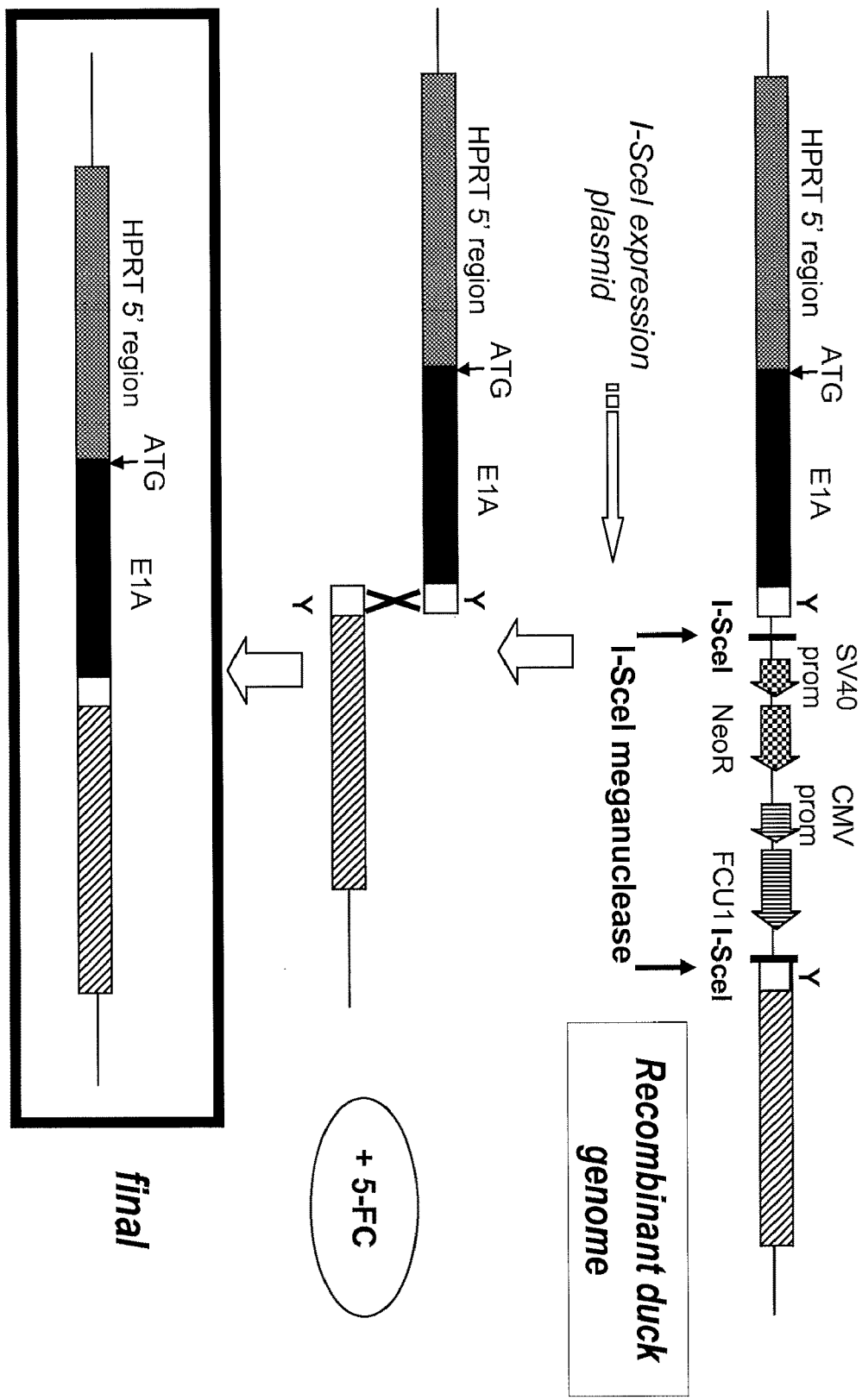

FIG. 3: Schematic representation of the elimination of the first and the third selection marker from the genome of the immortalized cell obtained by the process of the invention.

Figure 4:
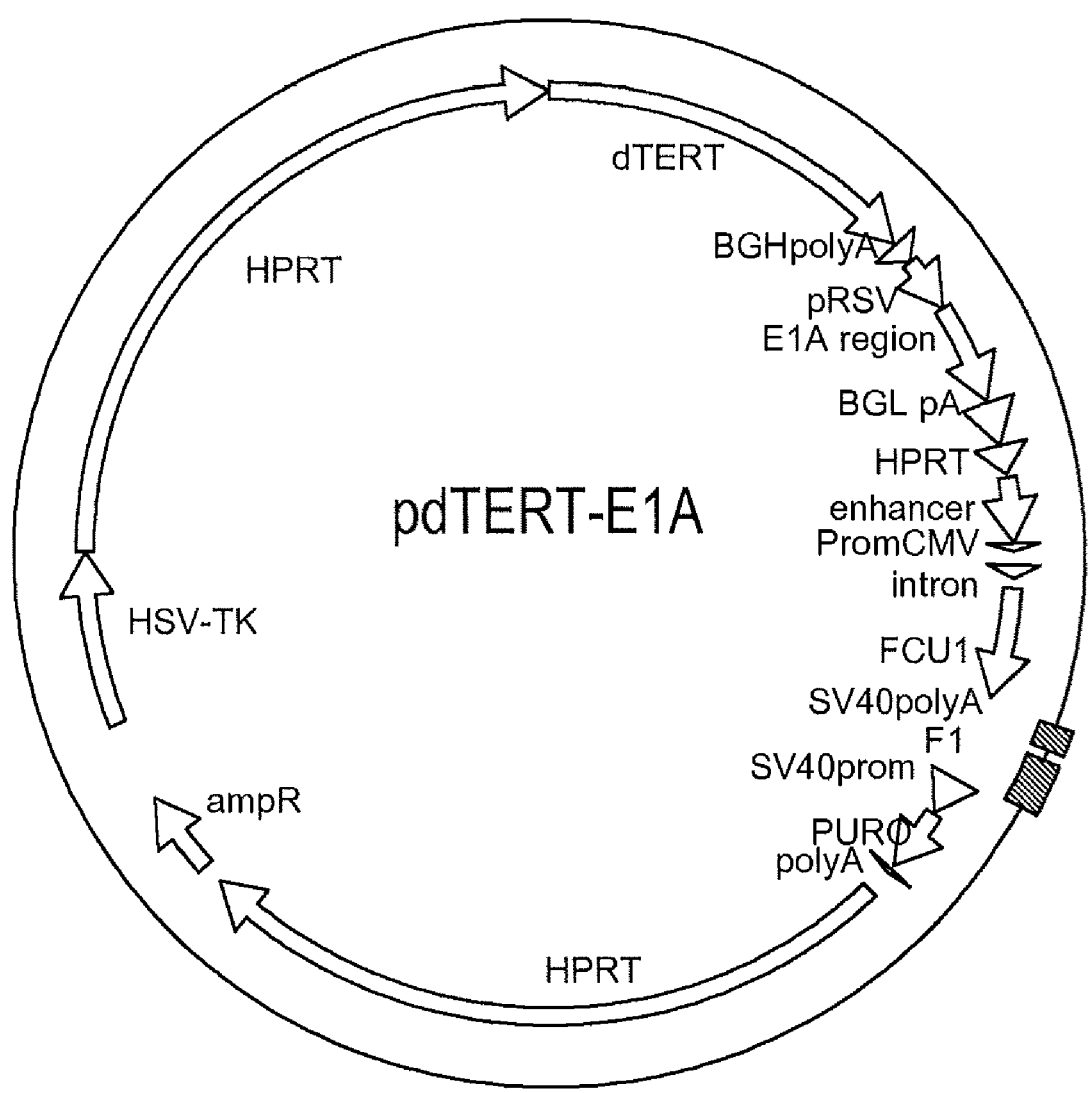

FIG. 4: Vector comprising a gene coding the *Cairina moschata* telomerase reverse transcriptase gene and the E1A nucleic acid sequence.

EXAMPLES

Example 1

Establishment of an Immortalized Avian Cell Line Comprising an E1A Nucleic Acid Sequence A. Plasmid Constructs.
A-1. Plasmid Constructs for Random Insertion.

A plasmid sharing no specific sequence of homology with the *Cairina moschata* genome (plasmid E1A) has been used for this purpose (FIG. 1).

A-2. Plasmid Constructs for Targeted Insertion.

A plasmid comprising two 5 kb fragments homologous to the *Cairina moschata* HPRT gene surrounding the E1A nucleic acid sequence (SEQ ID No:1) and two selection markers has been constructed. The HPRT gene encoding for the hypoxanthine guanine phosphoryl transferase has been selected as an adequate site for the constitutive expression of the E1A nucleic acid sequence.

These two selection marker are the FCU1 gene (Erbs et al. Cancer Res. 2000. 15. 60:3813-22) under the control of a CMV promoter (Thomsen et al. P.N.A.S. 1984. 81. 3:659-63) and the Neomycin (or Puromycin) resistance gene placed under the control of a SV40 promoter. Neomycin (or Puromycin) resistance and FCU-1 expression cassette are surrounded by Sce1 cleavage sites that allow the elimination of the selection cassettes from the final cell line. Outside of the HPRT gene arms is inserted a selection marker coding the HSVTK driven by an RSV promoter (FIG. 2).

B. Preparation of CEC Batch from *Cairina Moschata* Eggs and Subpopulations Description.

B.1 Preparation of CEC Batch from 12 old *Cairina moschata* Eggs and Subpopulations Description.

25 fertilized SPF eggs are incubated at 37.5° C. Eggs are opened after 12 days incubation following available protocol.

23 embryos are minced, washed once in Phosphate Buffered Saline-Dulbecco (PBS) and dissociated in TrypLE Select (Invitrogen) 5 hours at room temperature.

After low speed centrifugation cells are resuspended in Basal Medium Eagle (MBE) supplemented with 10% fetal calf serum (FCS), gentamycine 0.04 g/L, seeded in 500 cm² triple flasks and incubated at 37° C. 5% $CO_2$.

After 24 h the confluent cells are removed from the flasks using TrypLE Select (5 mL/triple flask), part of the cells were reseeded in 175 cm² flasks for second passage. The remaining cells were concentrated at $10^7$ cell/mL in appropriate media (60% BME, 30% FCS and 10% DMSO) and frozen in a isopropyl alcohol regulated container (NALGENE.®. "Mr. Frosty" 1° C. freezing. Container) at −80° C. prior to transfer in liquid azote for long term storage, constituting the initial cell bank (50×1.5·$10^7$ cells/vial, 44×1·$10^7$ cells/vial).

Cells remained in culture are passaged classically up to 18 passages, during the 3 first passages non attached cells are collected by low centrifuging the conditioned media, reseeded and further passaged in the same way as the initial culture.

Subpopulations, displaying characteristic different morphological features, have been reproducibly isolated during the culture's lifespan.

B.2. Preparation of CEC Batch from 19 Old *Cairina moschata* Eggs and Subpopulations Description.

29 fertilized SPF *Cairina moschata* eggs obtained from AFFSSA Ploufragan are incubated at 37.5° C. in humid atmosphere.

Eggs are opened after 19 days and embryos sterilely extracted. 20 embryos are beheaded, limbs removed as well as the liver used for other cell preparation. The embryonic torsi are minced, washed once in PBS Dulbecco (Sigma, Réf. D8537, Lot 46K2428) and dissociated in 500 mL TrypLE Select (Gibco, Réf. 12563, Lots 1319986 and 1339844) 2 hours at 37° C.

After 5 minutes 2000 rpm centrifugation cells are resuspended in BME (Basal Medium Eagle, Gibco, Réf. 41010, Lot 8270) supplemented with 10% fetal calf serum (JRH, Réf. 12003-1000M, Lot. 5A0102, Code TG P4001Q), gentamycin 0.04 g/L and L-Glutamine 4 mM. A final volume of 1.5 L (1.9·$10^6$ cell/mL) suspension is seeded in 10 triple flasks (500 cm²) and incubated at 37° C. 5% $CO_2$.

After 24 h the confluent cells are washed with PBS and removed from the flasks using TrypLE Select. Cells are counted and centrifuged 4-5 minutes at 2000 rpm. The pellet is concentrated at 5·$10^6$ or $10^7$ cell/mL in appropriate media (60% BME, 30% FCS and 10% DMSO). The suspension is filled in cryovials (Nunc) and frozen at −80° C. with a meanwhile 2 h step at −20° C., prior to transfer in liquid nitrogen for long term storage, constituting the primary cell bank (110 cryovials, $10^7$ cells/vial) of CETC19 p1 (Duck Torso Embryonic Cells, 19 days old embryos, passage 1).

In a preferred embodiment of the present invention, the preparation of CEC batch from *Cairina moschata* eggs is performed according to alternative B.2. (from 19 old *Cairina moschata* eggs).

C. Methods of Transfection.

A large number of transfection methods are known in the art to introduce a vector capable of directing expression of a nucleotide sequence of interest. A non limiting list of these methods is listed hereafter: $CaPO_4$ precipitation, electroporation, lipofectin transfection method. A given example is based on $CaPO_4$ precipitation procedure.

Cells should be around 80-50% confluency. The medium is change two hours before $CaPO_4$/DNA addition. The 30 µg DNA is resuspended in 31 µl 2M $CaCl_2$-161.3 mM Tris pH 7.6. $H_2O$ is added to a final volume of 0.5 ml.

Then, 2 alternatives:

a) Per transfection, 0.5 ml of 2×HEBS is distributed in 15 ml sterile Falcon tube and the DNA solution is added drop wise while gently vortexing or bubbling the DNA solution in. The solution should become milky. The mix is let stand at room temperature for 10-30 min. Then pipette in and out once with sterile pipette in tissue culture cabinet to break up flakes and apply drop wise to cells. Cells are then incubated between 6 hours to overnight at 37° C. A fine precipitate should cover the cell surface. In order to complete the transfection procedure warm up to 37° C. the glycerol shock solution. The medium is aspirate off, 5 ml BME is added to wash the cell layer, the medium is then aspirate off and 1 ml glycerol shock solution is added for 2 min or less. Subsequently 10 ml BME are added gently to dilute the glycerol and BME-glycerol is completely removed. 10 ml of desired medium is then added and plates are incubated at the appropriate temperature.

or b) Per transfection, 0.5 ml of 2×HEBS is distributed in 15 ml sterile Falcon tube and the DNA solution is added drop wise while gently vortexing or bubbling the DNA solution in. The solution should become milky. The mix is let stand at room temperature for 10-30 min. Then pipette in and out once with sterile pipette in tissue culture cabinet to break up flakes and apply drop wise to cells. A fine precipitate should cover the cell surface. Cells are then incubated between 6 hours to overnight at 37° C.

In a preferred embodiment of the present invention, the transfection (CaPO$_4$ precipitation) is performed according to alternative b).

D. Methods of Selection.

D-1. Method of Selection for Random Insertion:

Selection pressure is applied 48 to 72 hours after transfection: cells are dissociated with TrypLE select, low speed centrifuged and reseeded in BME with FCS 10% and G418 800 μg/mL, preferably 500 μg/mL (and optionally Ganciclovir 25 μg/mL, preferably 10 μg/mL).

Cells are serially passaged until individual growing clones can be isolated.

D-2. Method of Selection for Targeted Insertion:

Selection pressure is applied 48 to 72 hours after transfection: cells are dissociated with TrypLE select, low speed centrifuged and reseeded in BME with FCS 10%; Ganciclovir 25 μg/mL, preferably 10 μg/mL; and G418 800 μg/mL, preferably 500 μg/mL (or Puromycin 0.5 μg/mL).

Cells are serially passaged until individual growing clones can be isolated.

Cell clones are subsequently transfected with a meganuclease I-SceI expression plasmid following the method described below.

To select the elimination of the selection markers 5-Fluorocytosine (5-FC) is applied 48 hours after transfection: cells are dissociated with TrypLE select, low speed centrifuged and reseeded in media with 5-FC concentration ranging from $10^{-3}$ to $10^{-7}$ M and maintained G418 (or Puromycin)/Ganciclovir selection (BME with FCS 10%; 5-FC Ganciclovir 25 μg/mL, preferably 10 μg/mL; and G418 800 μg/mL, preferably 500 μg/mL (or Puromycin 0.5 μg/mL) (FIG. 3).

Example 2

Establishment of an Immortalized Avian Cell Line Comprising an E1A Nucleic Acid Sequence and a Recombinant Telomerase Reverse Transcriptase Nucleic Acid Sequence A. Plasmid Constructs.

A-1. Plasmid Constructs for Random Insertion.

A plasmid sharing no specific sequence of homology with the *Cairina moschata* genome has been used for this purpose.

A-2. Plasmid Constructs for Targeted Insertion.

A plasmid (plasmid dTERT-E1A) comprising two 5 kb fragments homologous to the *Cairina moschata* HPRT gene surrounding the *Cairina moschata* telomerase reverse transcriptase gene (SEQ ID No:3), the E1A nucleic acid sequence (SEQ ID No:1) and two selection markers has been constructed. The HPRT gene encoding for the hypoxanthine guanine phosphoryl transferase has been selected as an adequate site for the constitutive expression of the E1A nucleic acid sequence.

These two selection marker are the FCU1 gene (Erbs et al. Cancer Res. 2000. 15. 60:3813-22) under the control of a CMV promoter (Thomsen et al. P.N.A.S. 1984. 81. 3:659-63) and the Puromycin resistance gene placed under the control of a SV40 promoter. Puromycin resistance and FCU-1 expression cassette are surrounded by Sce1 cleavage sites that allow the elimination of the selection cassettes from the final cell line. Outside of the HPRT gene arms is inserted a selection marker coding the HSVTK driven by an RSV promoter (FIG. 4).

B. Preparation of CEC Batch from 19 Old *Cairina moschata* eggs and Subpopulations Description.

29 fertilized SPF *Cairina moschata* eggs obtained from AFFSSA Ploufragan are incubated at 37.5° C. in humid atmosphere.

Eggs are opened after 19 days and embryos sterilely extracted. 20 embryos are beheaded, limbs removed as well as the liver used for other cell preparation. The embryonic torsi are minced, washed once in PBS Dulbecco (Sigma, Réf. D8537, Lot 46K2428) and dissociated in 500 mL TrypLE Select (Gibco, Réf. 12563, Lots 1319986 and 1339844) 2 hours at 37° C.

After 5 minutes 2000 rpm centrifugation cells are resuspended in BME (Basal Medium Eagle, Gibco, Réf. 41010, Lot 8270) supplemented with 10% fetal calf serum (JRH, Réf. 12003-1000M, Lot. 5A0102, Code TG P4001Q), gentamycin 0.04 g/L and L-Glutamine 4 mM. A final volume of 1.5 L ($1.9 \cdot 10^6$ cell/mL) suspension is seeded in 10 triple flasks (500 cm$^2$) and incubated at 37° C. 5% CO$_2$.

After 24 h the confluent cells are washed with PBS and removed from the flasks using TrypLE Select. Cells are counted and centrifuged 4-5 minutes at 2000 rpm. The pellet is concentrated at $5 \cdot 10^6$ or $10^7$ cell/mL in appropriate media (60% BME, 30% FCS and 10% DMSO). The suspension is filled in cryovials (Nunc) and frozen at −80° C. with a meanwhile 2 h step at −20° C., prior to transfer in liquid nitrogen for long term storage, constituting the primary cell bank (110 cryovials, $10^7$ cells/vial) of CETC19 p1 (Duck Torso Embryonic Cells, 19 days old embryos, passage 1).

C. Methods of Transfection.

A large number of transfection methods are known in the art to introduce a vector capable of directing expression of a nucleotide sequence of interest. A non limiting list of these methods is listed hereafter: CaPO$_4$ precipitation, electroporation, lipofectin transfection method. A given example is based on electroporation.

Transfection is performed using Amaxa's Nucleofector device and the Basic Fibroblast kit (Amaxa, Cat N° VPI-1002). Cells are centrifuged 10 min at 700 rpm (100 g) and resuspended in Basic Nucleofector Solution (100 μL per 10$^6$ cells); 100 μL suspension are mixed with 3 to 6 μg DNA and transferred to a cuvette placed in the Nucleofector (U-12 program). After electroporation the sample is transferred to a 6 cm culture dish, filled with 5 mL culture media, preequilibrated in the 37° C./5% CO$_2$ incubator. After incubation over night at 37° C. 5% CO$_2$ culture media is renewed and incubation pursued.

D. Methods of Selection.

D-1. Method of Selection for Random Insertion:

Selection pressure is applied 48 to 72 hours after transfection: cells are dissociated with TrypLE select, low speed centrifuged and reseeded in BME with FCS 10%, Ganciclovir 25 μg/mL, preferably 10 μg/mL; and G418 800 μg/mL, preferably 500 μg/mL.

Cells are serially passaged until individual growing clones can be isolated.

D-2. Method of Selection for Targeted Insertion:

Selection pressure is applied 48 to 72 hours after transfection: cells are dissociated with TrypLE select, low speed centrifuged and reseeded in BME with FCS 10%; Ganciclovir 25 µg/mL, preferably 10 µg/mL; and Puromycin 0.5 µg/mL.

Cells are serially passaged until individual growing clones can be isolated.

Cell clones are subsequently transfected with a meganuclease I-SceI expression plasmid following the method described below.

To select the elimination of the selection markers 5-Fluorocytosine (5-FC) is applied 48 hours after transfection: cells are dissociated with TrypLE select, low speed centrifuged and reseeded in media with 5-FC concentration ranging from $10^{-3}$ to $10^{-7}$ M and maintained Puromycin/Ganciclovir selection (BME with FCS 10%; 5-FC Ganciclovir 25 µg/mL, preferably 10 µg/mL; and Puromycin 0.5 µg/mL).

BIBLIOGRAPHY

Scholl et al., 2003, J Biomed Biotechnol., 2003, 3, 194-201
U.S. Pat. No. 5,879,924
WO2005007840
Ivanov et al. Experimental Pathology And Parasitology, 4/2000 Bulgarian Academy of Sciences
Ivanov et al. Experimental Pathology And Parasitology, 4/6 2001 Bulgarian Academy of Sciences
Fallaux, F. J. et al., Hum. Gene Ther. 9: 1909-17 (1998);
Graham, F. L. et al., J. Gen. Virol. 36: 59-74 (1977)
Guilhot, C. et al., Oncogene 8: 619-24 (1993)
WO 98/08489,
WO 98/17693,
WO 98/34910,
WO 98/37916,
WO 98/53853,
EP 890362
WO 99/05183
Lathe et al., 1987, Gene 57, 193-201
Lupton and Levine, 1985, Mol. Cell. Biol. 5, 2533-2542;
Yates et al., Nature 313, 812-815
Summers and Sherrat, 1984, Cell 36, 1097-1103
Nunes-Duby, S. et al (1998) Nucleic Acids Res. 26:391-406
Sternberg, N. et al. (1986) J. Mol. Biol. 187: 197-212
Belfort and Roberts ((1997) Nucleic Acids Research 25:3379-3388
Jayaram, Proc Natl Acad Sci USA. 1985 September; 82(17):5875-9;
Senecoff et al., J Mol. Biol. 1988 May 20; 201(2):405-21
Panigrahi et al., Nucleic Acids Res. 1992 Nov. 25; 20(22):5927-35
Snaith et al. Gene. 1996 Nov. 21; 180(1-2):225-7
Caruso et al., 1993, Proc. Natl. Acad. Sci. USA 90, 7024-7028;
Culver et al., 1992, Science 256, 1550-1552;
Ram et al., 1997, Nat. Med. 3, 1354-1361;
Wei et al., 1994, Human Gene Therapy 5, 969-978
Sorscher et al., 1994, Gene Therapy 1, 233-238
Mzoz and Moolten, 1993, Human Gene Therapy 4, 589-595
WO9954481
WO2005007857
McIvor et al., 1987, Mol. Cell. Biol. 7, 838-848
Tabin et al., 1982, Mol. Cell. Biol. 2, 416-436
Takebe et al., 1988, Mol. Cell. 8, 466-472
EP 06 36 0047.2
French applications 94 08300 and 97 05203, published under n° FR2722208 and FR2762615 respectively
Graham and Prevect, 1991, in Methods in Molecular Biology, Vol 7, p 109 128; Ed: E. J. Murey, The Human Press Inc
Lamb et al, Eur. J. Biochem., 1985, 148, 265-270
Mullen et al (1922) PNAS 89, 33
Moolten (1986) Cancer Res. 46, 5276;
Ezzedine et al (1991) New Biol 3, 608
Erbs et al. Cancer Res. 2000. 15. 60:3813-22
Thomsen et al. P.N.A.S. 1984. 81. 3:659-63

---

The invention claimed is:

1. An immortalized avian cell containing an E1A nucleic acid sequence, wherein said cell is obtained by a process which comprises the step of transfecting the cell with a non-viral vector comprising said E1A nucleic acid sequence and wherein said cell is devoid of an E1B nucleic acid sequence and wherein said cell further comprises a nucleic acid sequence encoding a recombinant telomerase reverse transcriptase.

2. The immortalized cell as defined by claim 1, wherein said E1A nucleic acid sequence is inserted into the HPRT gene of said avian cell.

3. The immortalized cell as defined by claim 2, wherein said E1A nucleic acid sequence is operably linked to said cell's endogenous HPRT promoter.

4. The immortalized cell as defined by claim 1, wherein said cell is obtained from an animal belonging to the Anatidae family.

5. The immortalized cell as defined by claim 4, wherein said animal belongs to the *cairina moschata* species or the *Anas platyrhynchos* species.

6. The immortalized cell as defined by claim 1, wherein said E1A nucleic acid sequence includes the sequence encoding the two major RNAs 13S and 12S.

7. The immortalized cell as defined by claim 6, wherein said E1A nucleic acid sequence has at least 60% nucleic acid sequence identity to SEQ ID NO:1.

8. The immortalized cell as defined by claim 7, wherein said E1A nucleic acid sequence is as set forth in SEQ ID NO:1.

9. The immortalized cell as defined by claim 1, wherein said nucleic acid sequence encoding a recombinant telomerase reverse transcriptase has at least 70% nucleic acid sequence identity to SEQ ID NO:3.

10. The immortalized cell as defined by claim 1, wherein said nucleic acid sequence encoding a recombinant telomerase reverse transcriptase is as set forth in SEQ ID NO:3.

11. The immortalized cell as defined by claim 1, further comprising a nucleic acid sequence encoding a substance of interest.

12. The immortalized cell as defined by claim 1, further comprising a complementation cassette allowing the propagation of a defective virus.

13. An isolated cell developed from, differentiated from or have an ancestor from an immortalized cell according claim 1.

* * * * *